United States Patent
Arcand et al.

(10) Patent No.: US 8,225,474 B2
(45) Date of Patent: Jul. 24, 2012

(54) STENT CRIMPING DEVICE

(75) Inventors: Benjamin Arcand, Minneapolis, MN (US); Ryan Welty, Blaine, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1090 days.

(21) Appl. No.: 12/130,870

(22) Filed: May 30, 2008

(65) Prior Publication Data

US 2009/0299453 A1     Dec. 3, 2009

(51) Int. Cl.
     *B25B 27/14*     (2006.01)
(52) U.S. Cl. ............... 29/272; 29/270; 29/271; 29/280; 29/282; 29/283
(58) Field of Classification Search .......... 29/270, 29/271, 272, 280, 282, 283
     See application file for complete search history.

(56) References Cited

U.S. PATENT DOCUMENTS

| | | | |
|---|---|---|---|
| 5,437,083 A | 8/1995 | Williams et al. | |
| 5,546,646 A | 8/1996 | Williams et al. | |
| 5,738,674 A | 4/1998 | Williams et al. | |
| 5,746,764 A | 5/1998 | Green et al. | |
| 5,911,452 A | 6/1999 | Yan | |
| 5,931,851 A | 8/1999 | Morales | |
| 5,944,735 A * | 8/1999 | Green et al. .......... | 606/194 |
| 5,972,028 A | 10/1999 | Rabenau et al. | |
| 5,974,652 A | 11/1999 | Kimes et al. | |
| 5,992,000 A | 11/1999 | Humphrey et al. | |
| 6,009,614 A | 1/2000 | Morales | |
| 6,240,615 B1 | 6/2001 | Kimes et al. | |
| 6,360,577 B2 | 3/2002 | Austin | |
| 6,387,117 B1 | 5/2002 | Arnold, Jr. et al. | |
| 6,387,118 B1 | 5/2002 | Hanson | |
| 6,618,921 B1 * | 9/2003 | Thornton .......... | 29/270 |
| 6,745,445 B2 | 6/2004 | Spilka | |
| 6,823,576 B2 | 11/2004 | Austin | |
| 6,920,674 B2 | 7/2005 | Thornton | |
| 7,021,114 B2 | 4/2006 | Perreault | |
| 7,096,554 B2 | 8/2006 | Austin et al. | |
| 7,225,518 B2 | 6/2007 | Eidenschink et al. | |
| 2005/0033404 A1 | 2/2005 | Eidenschink | |
| 2006/0036310 A1 | 2/2006 | Spencer et al. | |
| 2008/0028594 A1 * | 2/2008 | Lafont et al. .......... | 29/516 |

FOREIGN PATENT DOCUMENTS

| | | |
|---|---|---|
| DE | 29808141 U1 | 11/1998 |
| EP | 0630623 | 12/1994 |
| WO | 9819633 | 5/1998 |
| WO | 9953864 | 10/1999 |
| WO | 9953866 | 10/1999 |
| WO | 9955255 | 11/1999 |
| WO | 9956668 | 11/1999 |
| WO | 2004039237 | 5/2004 |
| WO | 2005099967 | 10/2005 |

* cited by examiner

*Primary Examiner* — Lee D Wilson
*Assistant Examiner* — Shantese McDonald
(74) *Attorney, Agent, or Firm* — Seager Tufte & Wickhem LLC

(57) ABSTRACT

A crimping fixture for crimping a stent onto a balloon of a catheter is disclosed. The crimping fixture includes a flexible elastomeric body having a crimping lumen and one or more inflation lumens extending through the flexible elastomeric body. The flexible elastomeric body is elastically stretched such that a pre-crimped stent may be placed in the crimping lumen. The inflation lumens are then pressurized with a fluid to impart an inward crimping force onto the stent to crimp the stent to a balloon.

14 Claims, 36 Drawing Sheets

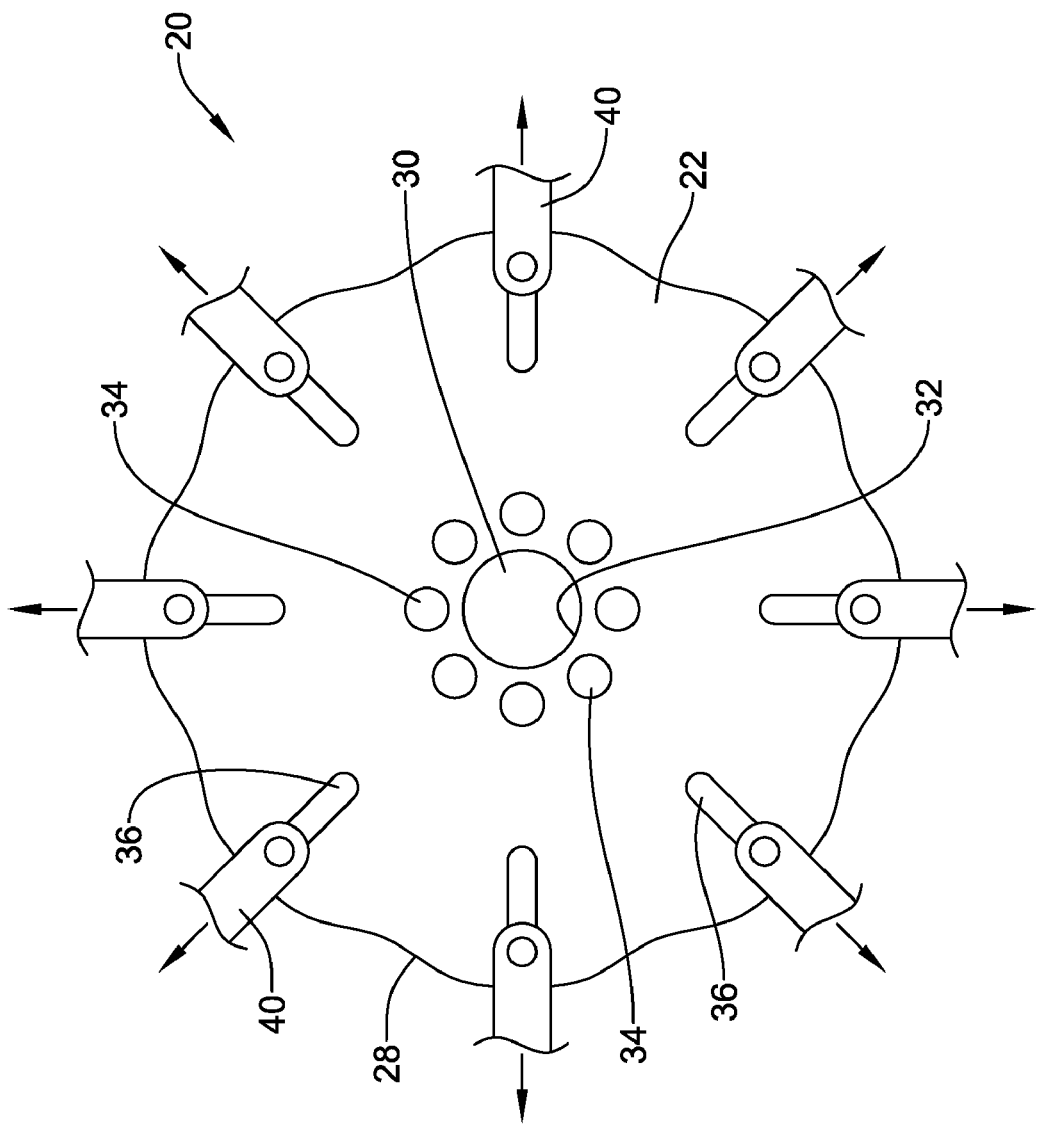

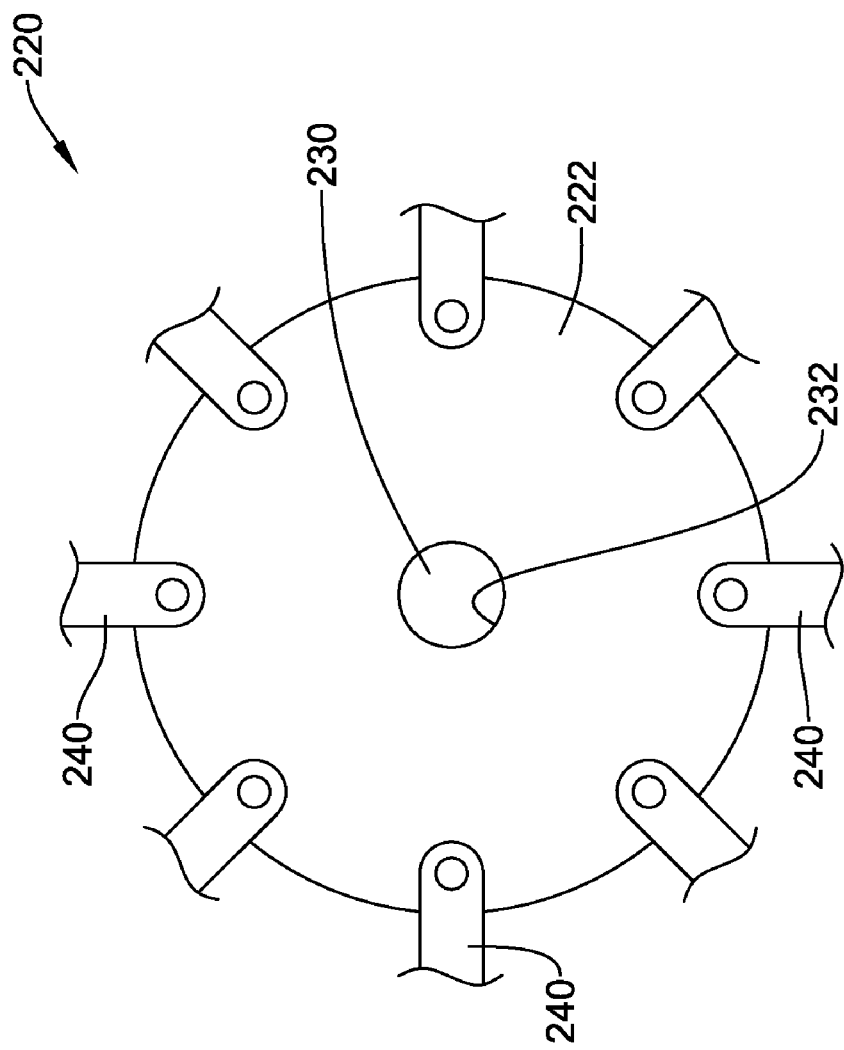

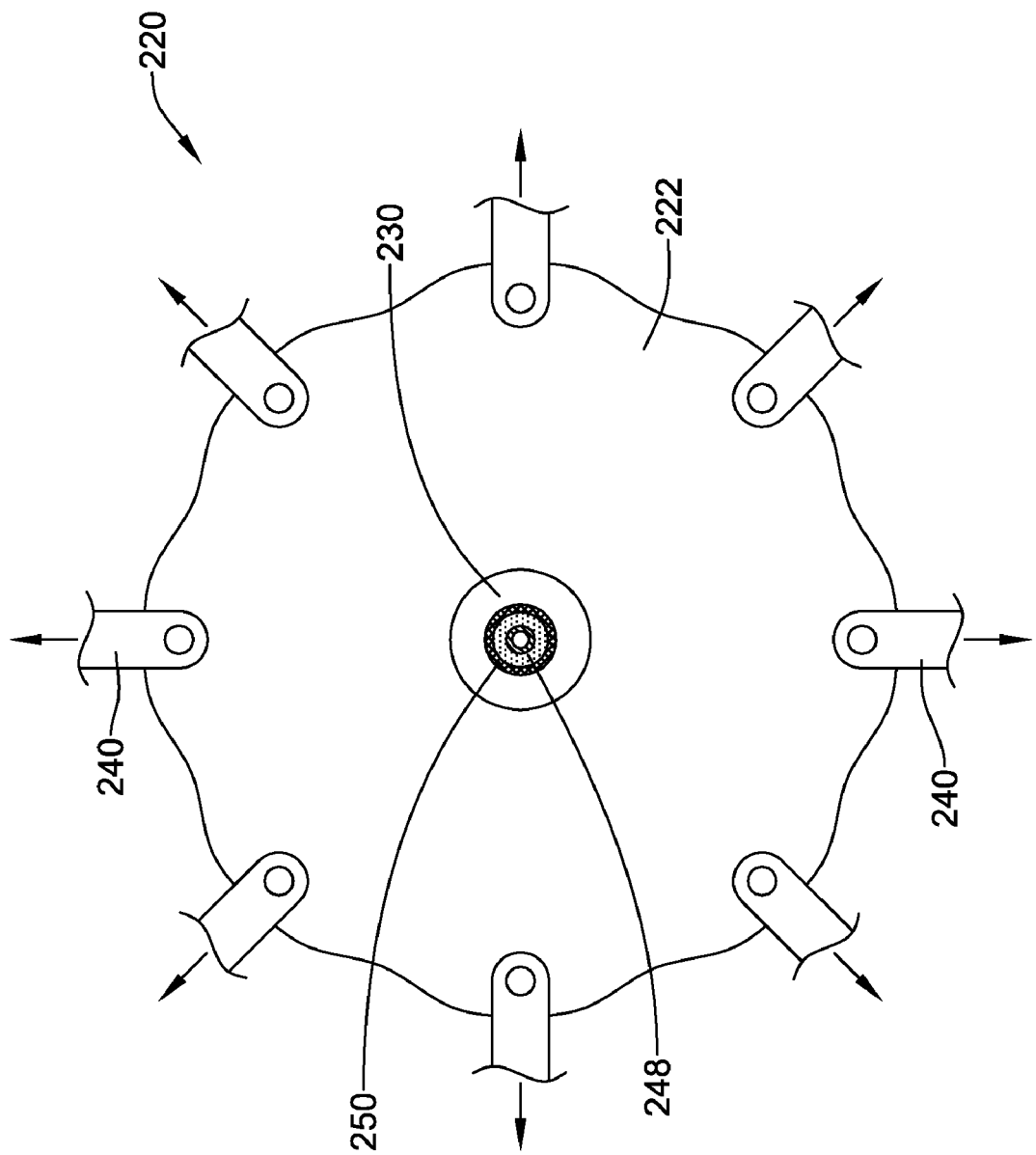

STENT CRIMPING DEVICE

TECHNICAL FIELD

The disclosure is directed to apparatus for crimping stents onto medical devices, such as catheter balloons. More particularly, the disclosure is directed to stent crimping devices, fixtures, machines, assemblies and methods of crimping stents onto balloons of balloon catheters or other medical devices.

BACKGROUND

Stents and stent delivery systems are utilized in a number of medical procedures and situations. A stent typically is a prosthesis introduced via a catheter into a lumen of a body vessel in a configuration having a generally reduced diameter and then expanded to the diameter of the vessel. A stent delivery system includes a stent loaded onto the balloon of a balloon catheter. Stent delivery systems are commonly used during percutaneous transluminal coronary angioplasty (PTCA) procedures to deploy a stent inside a vessel proximate a lesion to support and reinforce the vessel walls while maintaining the vessel in an open, unobstructed condition.

Prior to use during a medical procedure, a stent is normally securely crimped onto the balloon of a balloon catheter. Stent crimping refers to reducing the cross-sectional dimensions or profile (e.g., the diameter) of a stent prior to use. Several techniques for crimping a stent onto a balloon of a balloon catheter have been developed. Some such crimping devices and methods are disclosed in U.S. Pat. Nos. 7,021,114, 6,920, 674, 6,823,576, 6,387,118, 6,387,117, 6,360,577, and 5,992, 000, the disclosures of which are incorporated herein by reference. However, in some instances these techniques have been found to result in the application of undesired uneven forces being applied to the stent and/or distortion of the desired cross-sectional shape of the stent, as well as other possible undesirable effects.

Therefore, it is desirable to develop stent crimping apparatus, assemblies and methods for more uniformly crimping a stent onto the balloon of a balloon catheter, while minimizing or eliminating distortion of the stent. For example, it may be desirable to generate iso-static forces acting on a stent during a crimping process. Additionally, it may be desirable to accommodate dissimilarities in the shape and/or regions of a stent (e.g., either circular/symmetrical stents and/or non-circular/non-symmetrical stents such as bifurcated stents) by optimally generating omni-directional forces, normal at all points of contact on the outer perimeter of the stent, during a crimping process.

SUMMARY

The disclosure is directed to several alternative designs, materials and methods of manufacturing medical device structures and assemblies.

Accordingly, one illustrative embodiment is a crimping member for crimping a stent onto a balloon of a catheter or other medical device. The crimping member includes an elongate body formed of an elastomeric material which can be stretched between a relaxed state in which the elongate body is not placed in tension and an elastically stretched state in which the elongate body is placed in tension. The elongate body includes a crimping lumen which may have a first diameter in the relaxed state and a second diameter greater than the first diameter in the elastically stretched state, wherein the first diameter of the crimping lumen of the elongate body is less than the pre-crimped diameter of a stent for placement within the crimping lumen.

Another illustrative embodiment is a crimping fixture for crimping a stent onto a balloon of a catheter or other medical device. The crimping fixture includes an elongate body formed of an elastomeric material allowing elastic deformation of the elongate body. The elongate body includes a crimping lumen and one or more inflation lumens spaced around the crimping lumen. The elastomeric material allows the elongate body to be elastically radially stretched in order to increase the diameter of the crimping lumen to receive a stent therein.

Yet another illustrative embodiment is an assembly for crimping a stent to a balloon of a catheter or other medical device. The assembly includes a catheter including an elongate shaft and a balloon secured to a distal region of the elongate shaft. A stent is loaded onto the balloon of the catheter. The assembly also includes a crimping member including an elongate body formed of an elastomeric material which may be elastically stretched between a relaxed state in which the crimping member is not placed in tension and an elastically stretched state in which the crimping member is placed in tension. The elongate member includes a crimping lumen for receiving the stent loaded onto the balloon of the catheter. The crimping lumen has a diameter in the relaxed state which is less than the pre-crimped diameter of the stent. The diameter of the crimping lumen in the relaxed state is also less than the post-crimped diameter of the stent.

Also disclosed is a method of crimping a stent onto a balloon of a catheter or other medical device. The method includes providing a crimping member including an elongate body formed of an elastomeric material. The elongate body includes a crimping lumen and one or more inflation lumens spaced around the crimping lumen. The crimping lumen is expanded to an elastically stretched diameter and a pre-crimped stent is placed in the elastically stretched crimping lumen. The crimping lumen is then allowed to elastically contract around the pre-crimped stent, thereby allowing the perimeter of the crimping lumen to conform to the perimeter of the pre-crimped stent. The one or more inflation lumens are then pressurized with a fluid in order to apply an omni-directional crimping force normal to the stent at all points of surface contact between the perimeter of the crimping lumen and the perimeter of the pre-crimped stent in order to crimp the stent onto a balloon. The crimping lumen may then be elastically stretched to remove the crimped stent from the crimping lumen.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which:

FIG. 5 is an end view of the stent crimping fixture of FIG. 2 with the stent crimping fixture in a radially expanded state;

FIG. 20A-20E illustrate an alternative stent crimping fixture and process;

Figure 1:
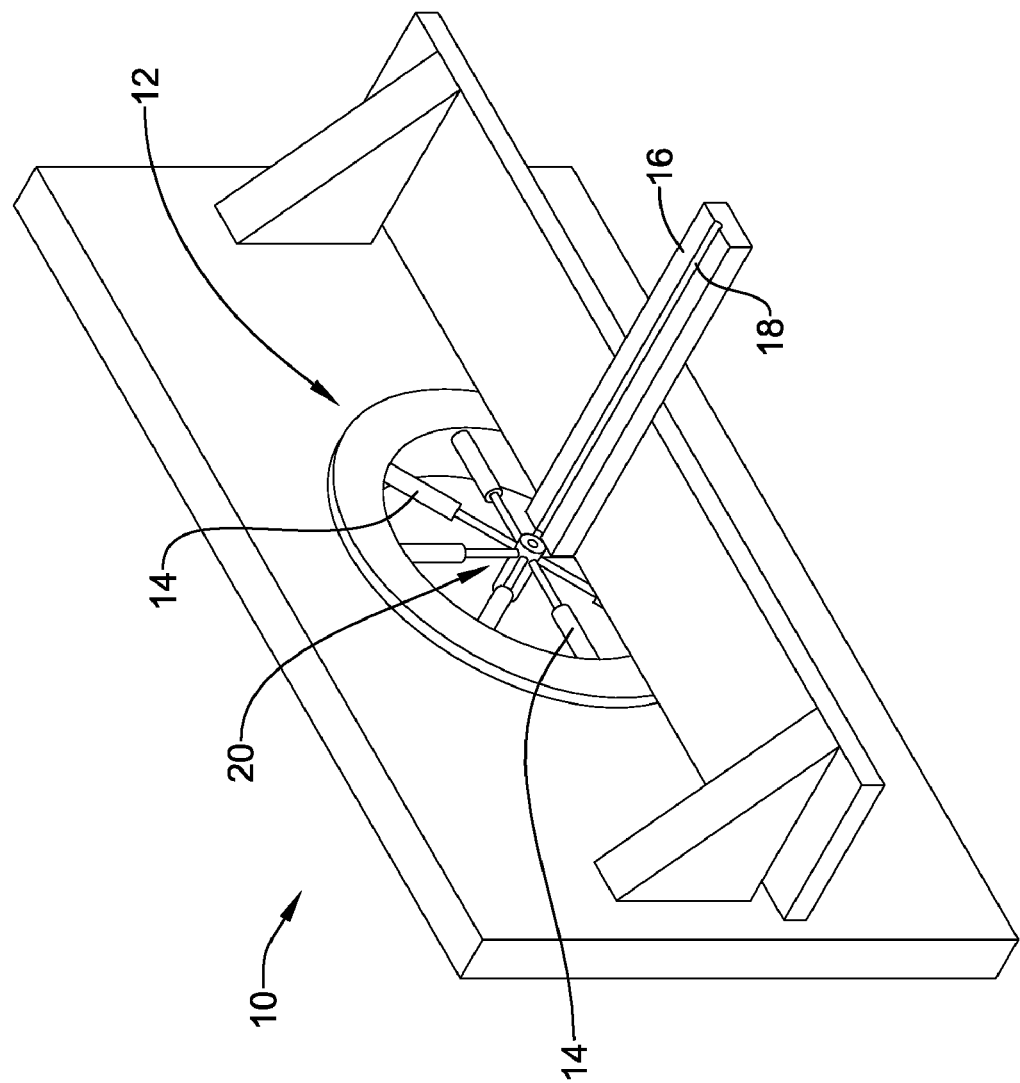
FIG. 1 is a perspective view of an illustrative stent crimping machine.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

An exemplary stent crimping machine 10 is illustrated in FIG. 1. The stent crimping machine 10 may be used to crimp a stent onto the balloon of a balloon catheter or other medical device. While the description illustratively discusses crimping a stent onto a balloon of a balloon catheter, one of skill in the art would understand that the stent crimping machine 10 may be used to crimp a stent onto any other desired medical device, such as a stent delivery device, prior to using the stent in a medical procedure.

As shown in FIG. 1, the stent crimping machine 10 may include a crimping fixture 20 for crimping a stent. The crimping fixture 20 may be centrally located within a mount 12 of the crimping machine 10. A plurality of radially actuatable cylinders 14, such as pneumatic or hydraulic cylinders, may be radially arranged around the crimping fixture 20. The plurality of cylinders 14 may be radially attached between the mount 12 and the crimping fixture 20. The plurality of cylinders 14 may be arranged to provide radially actuation of the crimping fixture 20 in the crimping machine. For example, the cylinders 14 may extend and/or contract in order to provide radial actuation of the crimping fixture 20. Other means of radially actuating the crimping fixture 20, such as one or more levers, cams, rods, stepper motors, or the like, are also contemplated A platform 16 may also be present. The platform 16 may include a channel 18 for supporting a catheter therein. Thus, a catheter may rest on the platform 16, such as in the channel 18. The channel 18 may be axially aligned with the center of the crimping fixture 20. Thus, the platform 16 may align a catheter, such that a portion of the catheter (e.g., balloon) is centrally located within the crimping fixture 20 during a crimping process. In some embodiments the platform 16 may be automated to align and/or load the catheter and/or stent within the crimping fixture 20.

The crimping fixture 20 may be further illustrated with reference to FIG. 2. The crimping fixture 20 may include a flexible elastomeric body 22 having a first end 24, a second end 26, and an outer peripheral surface 28 extending between the first end 24 and the second end 26. The flexible elastomeric body 22 has a length between the first end 24 and the second end 26, which, in some embodiments may be in the range of about 3 inches to about 7 inches or in the range of about 4 inches to about 6 inches. In some embodiments, the flexible elastomeric body 22 may resemble a cylindrical plug having one or more, or a plurality of lumens axially extending therethrough. In other embodiments, the flexible elastomeric body 22 may resemble another geometric body, or the flexible elastomeric body 22 may resemble a non-geometric body.

The flexible elastomeric body 22 may be a flexible elastomeric member, formed of an elastomeric material, such as an elastomeric polymer. The flexible elastomeric body 22 may be extruded, molded, such as by a conventional molding, automated molding, or lost material molding technique, or otherwise manufactured from an elastomeric material. For example, in some embodiments the flexible elastomeric body 22 may be formed of high density polyethylene (HDPE), polyether block amide (PEBA), nylon, urethane, silicone, latex, rubber, or other desired elastomeric material, or combinations of such materials in mixtures or discrete locations within the flexible elastomeric body 22, such as to control the elasticity or stiffness of the flexible elastomeric body 22. In some embodiments, the chosen elastomeric material may have an elastic deformation of at least 200% or more, 250% or more, 300% or more, 350% or more, or 400% or more. Thus, in some embodiments the flexible elastomeric body 22 may be elastically stretched to a size of 200% or more, 250% or more, 300% or more, 350% or more, or 400% or more of its unstretched size without rupture and/or plastic or permanent deformation.

In some embodiments, the flexible elastomeric body 22 may include one or more strands, sheets, or strips of fibrous material aligned in the radial direction in order to increase the radial stiffness of the flexible elastomeric body 22, yet preserve the circumferential elasticity of the flexible elastomeric body 22.

The flexible elastomeric body 22 may include a crimping lumen 30 defined by an inner surface 32 of the flexible elastomeric body 22. As discussed in more detail herein, the crimping lumen 30 may accommodate a stent during a crimping process. In some embodiments the crimping lumen 30 may be centrally located along a central longitudinal axis of the flexible elastomeric body 22. In some embodiments, the crimping lumen 30 may longitudinally extend from the first end 24 of the flexible elastomeric body 22 to the second end 26 of the flexible elastomeric body 22. In other embodiments, the crimping lumen 30 may longitudinally extend from the first end 24 of the flexible elastomeric body 22 toward the second end 26 of the flexible elastomeric body 22, but not all the way to the second end 26 of the flexible elastomeric body 22. In still other embodiments, the crimping lumen 30 may longitudinally extend from the second end 26 of the flexible elastomeric body 22 toward the first end 24 of the flexible elastomeric body 22, but not all the way to the first end 24 of the flexible elastomeric body 22.

The flexible elastomeric body 22 may also include one or more, or a plurality of inflation lumens 34. The inflation lumen(s) 34 may be arranged around the crimping lumen 30 such that the inflation lumen(s) 34 is/are radially outward from the crimping lumen 30, thus radially outward from the central longitudinal axis of the flexible elastomeric body 22. For example, as shown in FIG. 2, a plurality of inflation lumens 34 may be radially arranged around the crimping lumen 30 in a radial array. However, other arrangements are contemplated, including other arrangements disclosed herein. In some embodiments, the inflation lumens 34 may be symmetrically arranged around the crimping lumen 30. In other embodiments, the inflation lumens 34 may be asymmetrically arranged around the crimping lumen 30 to effectuate asymmetrical crimping of a stent onto a balloon. In some embodiments, the inflation lumens 34 may vary in size, shape and/or arrangement to effectuate asymmetrical crimping of a stent onto a balloon.

In some embodiments, the inflation lumen(s) 34 may longitudinally extend from the first end 24 of the flexible elastomeric body 22 to the second end 26 of the flexible elastomeric body 22. In other embodiments, the inflation lumen(s) 34 may longitudinally extend from the first end 24 of the flexible elastomeric body 22 toward the second end 26 of the flexible elastomeric body 22, but not all the way to the second end 26 of the flexible elastomeric body 22. In still other embodiments, the inflation lumen(s) 34 may longitudinally extend from the second end 26 of the flexible elastomeric body 22 toward the first end 24 of the flexible elastomeric body 22, but not all the way to the first end 24 of the flexible elastomeric body 22.

The flexible elastomeric body 22 may additionally include a plurality of expansion rod lumens 36 in which a plurality of expansion rods 38 (shown in FIG. 3) may be disposed. The expansion rods 38 may be attached to a plurality of arms 40, which in turn may be attached to the cylinders 14, as shown in FIG. 1. Only a portion of the arms 40 and expansion rods 38 are shown in FIG. 2 in an attempt to better illustrate the presence of the expansion rod lumens 36. One of ordinary skill would understand that in operation an expansion rod 38, along with its corresponding arm(s) 40, typically would be associated with each of the expansion rod lumens 36 of the flexible elastomeric body 22. The expansion rod lumens 36, the expansion rods 38 and/or the arms 40 may be radially arranged around the flexible elastomeric body 22. For example, the expansion rod lumens 36, the expansion rods 38 and/or the arms 40 may be radially arranged around the central longitudinal axis of the flexible elastomeric body 22 at a location radially outward of the inflation lumen(s) 34 and the crimping lumen 30.

The expansion rods 38, disposed in the plurality of expansion rod lumens 36, may be radially actuated with the cylinders 14, or other suitable actuation means, in order to elastically stretch the flexible elastomeric body 22 radially outward. For example, the plurality of arms 40 may be radially actuated outward, in turn directing the expansion rods 38 radially outward. Other means of radially actuating the flexible elastomeric body 22 in order to elastically stretch the flexible elastomeric body 22 radially outward are contemplated, including other arrangements disclosed herein.

Figure 3:
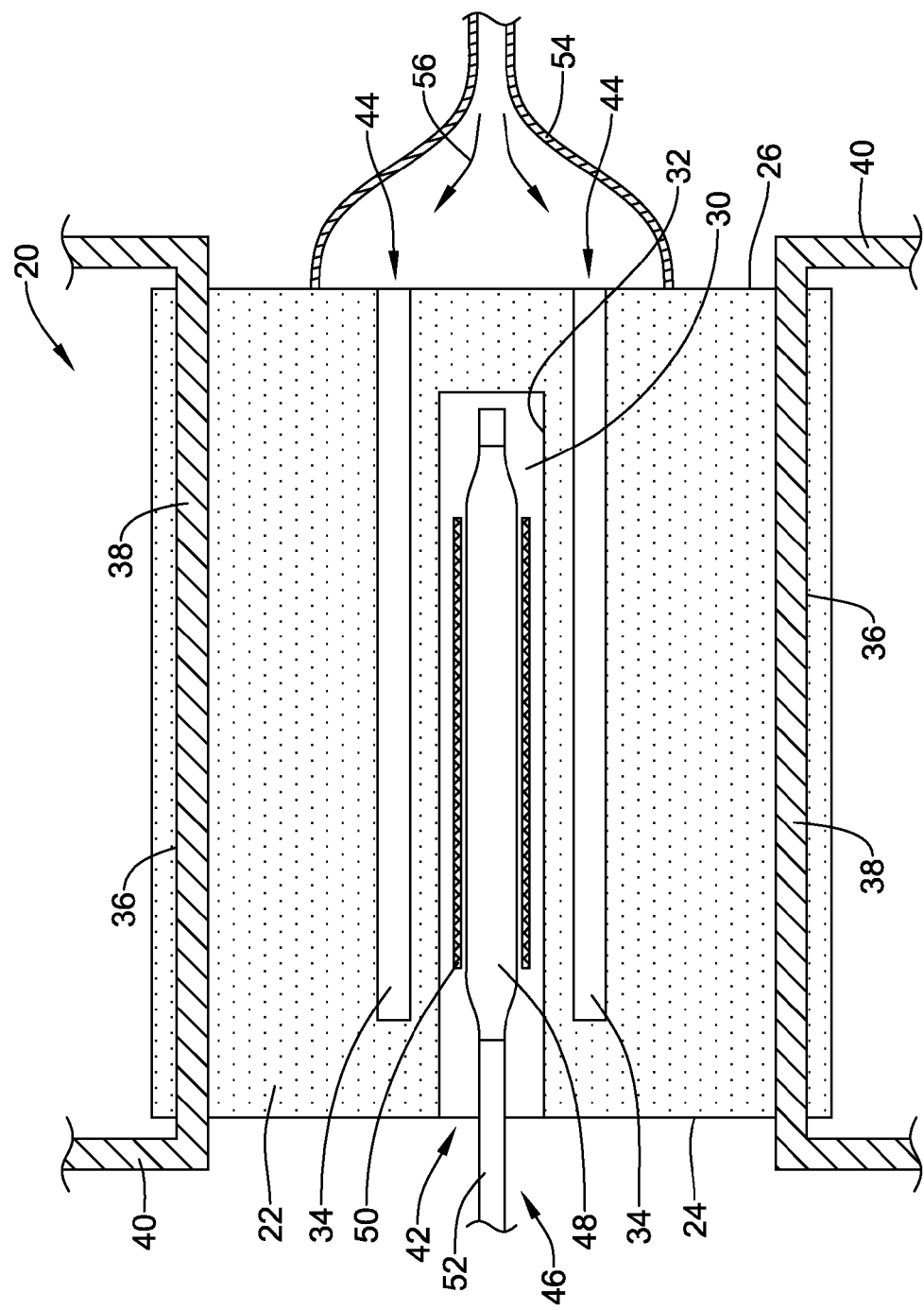
FIG. 3 is a longitudinal cross-sectional view of the stent crimping fixture of FIG. 2.

FIG. 3 is a longitudinal cross-sectional view of the crimping fixture 20 illustrating one possible arrangement of the various lumens of the flexible elastomeric body 22 and other components of the crimping fixture 20.

The expansion rods 38 may more readily be shown longitudinally extending through the expansion rod lumens 36 from the first end 24 of the flexible elastomeric body 22 to the second end 26 of the flexible elastomeric body 22. Arms 40 may be attached (e.g., detachably or permanently) to the expansion rods 38 to impart mechanical actuation of the expansion rods 28.

As shown in FIG. 3, the crimping lumen 30 may extend from an opening 42 at the first end 24 of the flexible elastomeric body 22 toward the second end 26 of the flexible elastomeric body 22, but not all the way to the second end 26 of the flexible elastomeric body 22. Furthermore, the inflation lumens 34 may extend from openings 44 at the second end 26 of the flexible elastomeric body 22 toward the first end 24 of the flexible elastomeric body 22, but not all the way to the first end 24 of the flexible elastomeric body 22. Thus, the crimping lumen 30 may be open to the first end 24 of the flexible elastomeric body 22 but not open to the second end 26, and the inflation lumens 34 may be open to the second end 26 of the flexible elastomeric body 22 but not open to the first end 24.

A medical device, such as a catheter 46 having a balloon 48 secured to a distal portion thereof is also shown in FIG. 3. A stent 50 may be disposed around the balloon 48 prior to a crimping process. During a crimping process, the stent 50 and the balloon 48 of the catheter 46 may be placed in the crimping lumen 30 of the flexible elastomeric body 22 in order to crimp the stent 50 to the balloon 48. As shown in FIG. 3, the elongate shaft 52 of the catheter 46 may extend out of the crimping lumen 30 beyond the opening 42 of the first side 24 of the flexible elastomeric body 22.

A nozzle 54, in fluid communication with a source of pressurized fluid (not shown) may be located at the second side 26 of the flexible elastomeric body 22. A fluid tight seal may be formed at the interface between the nozzle 54 and the second side 26 of the flexible elastomeric body 22. The nozzle 54 may be positioned over the openings 44 to the inflation lumens 34 such that the interior of the nozzle 54 may be in fluid communication with the inflation lumens 34. Thus, pressurized fluid 56, such as a non-compressible fluid or a compressed fluid, may be introduced into the inflation lumens 34 through the nozzle 54 from the source of pressurized fluid.

In some embodiments, during the crimping process the inflation lumens 34 may be pressurized to a pressure of about 6 atmospheres (ATM) or greater, about 8 ATM or greater, about 10 ATM or greater, about 12 ATM or greater, about 14 ATM or greater, or 16 ATM or greater. In some embodiments the inflation lumens 34 may be pressurized to a pressure in the range of about 6 ATM to about 16 ATM, in the range of about 8 ATM to about 14 ATM, or in the range of about 10 ATM to about 14 ATM.

As shown in FIG. 3, by having the crimping lumen 30 open to the first end 24 of the flexible elastomeric body 22, the catheter shaft 52 extending from the first end 24 will not interfere with the pressurization of the inflation lumens 34. Additionally, while having the inflation lumens 34 open to the second end 26 of the flexible elastomeric body 22, the nozzle 54 may be placed on the second end 26 of the flexible elastomeric body 22 without interfering with the catheter shaft 52. Furthermore, since the crimping lumen 30 is closed to the second end 26, pressurizing the inflation lumens 34 will not result in the crimping lumen 30 being pressurized by the pressurized fluid 56.

Figure 4:
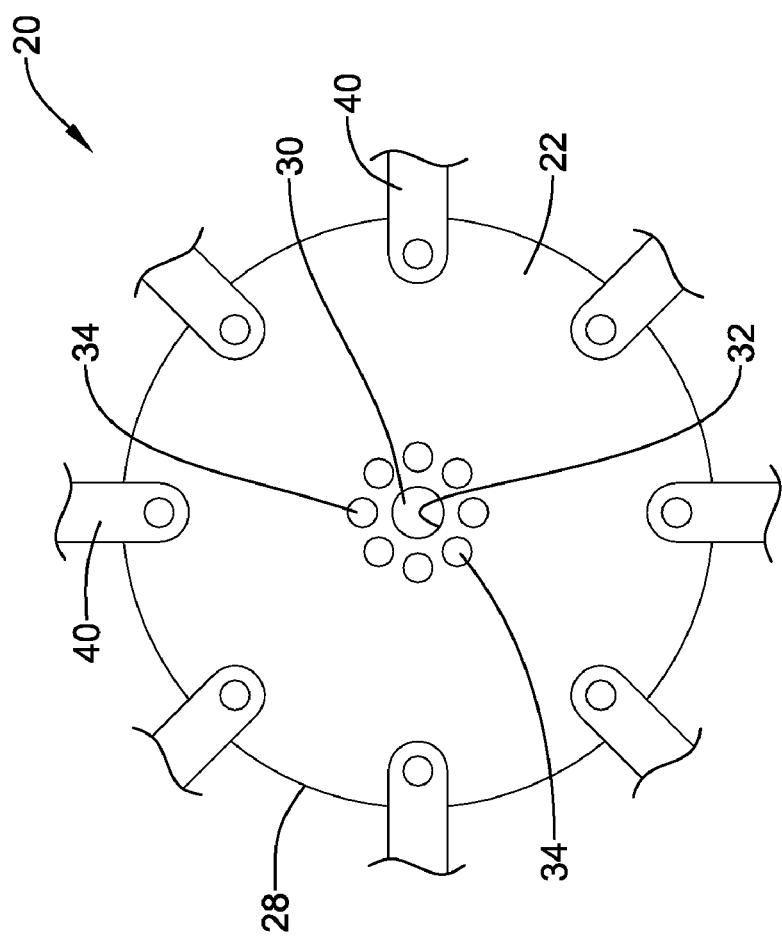
FIG. 4 is an end view of the stent crimping fixture of FIG. 2 with the stent crimping fixture in a radially retracted state.

FIGS. 4 and 5 are end views of the crimping fixture 20 in which the flexible elastomeric body 22 is in a relaxed, unstretched state and an elastically stretched or expanded state, respectively. As shown in FIG. 4, the plurality of arms 40 may be arranged in a radial array around the flexible elastomeric body 22. When the arms 40 are actuated radially outward, the flexible elastomeric body 22 is elastically stretched or expanded as shown in FIG. 5. The arrows of FIG. 5 illustrate the arms 40 actuating radially outward. When the flexible elastomeric body 22 is elastically stretched or expanded, the cross-sectional dimension (e.g., diameter) of the crimping lumen 30 and the cross-sectional dimension (e.g., diameter) of the inflation lumens 34 are increased in size. In some embodiments, the crimping lumen 30 may be increased from a diameter of less than 0.045 inches in the relaxed, unstretched state to a diameter of greater than 0.060 inches in the elastically stretched or expanded state. Other comparative dimensions are also possible in which the diameter of the crimping lumen 30 in the relaxed, unstretched state is less than the diameter of the crimping lumen 30 in the elastically stretched or expanded state. In some embodiments, the diameter of the crimping lumen 30 in the elastically stretched or expanded state may be 200% or more, 250% or more, or 300% or more than the diameter of the crimping lumen 30 in the relaxed, unstretched state.

As shown in FIGS. 4 and 5, the amount of elastomeric material of the flexible elastomeric body 22 radially inward from each of the inflation lumens 34 toward the crimping lumen 30 may be substantially less than the amount of elastomeric material of the flexible elastomeric body 22 radially outward from each of the inflation lumens 34 toward the outer periphery 28 of the flexible elastomeric body 22. By providing a greater amount of elastomeric material radially outward from each of the inflation lumens 34, inflation of the inflation lumens 34 tends to expand the inflation lumens 34 inward toward the crimping lumen 30. This tendency may direct the crimping forces generated through inflation of the inflation lumens 34 to a stent positioned in the crimping lumen 30. In some embodiments, the inflation lumens 34 may be located radially closer to the inner surface 32 of the crimping lumen 30 than to the outer peripheral surface 28 of the flexible elastomeric body 22.

In some embodiments when radially stretched, the expansion rod lumens 36 may be distorted (e.g., oblong shaped) such that a portion of the periphery of the expansion rod lumen 36 may be dissociated or disconnected from the expansion rod 38. In other embodiments, the expansion rods 38 may be adhered to, bonded to, or otherwise restrained to the inner surface of the expansion rod lumens 36, such that the entire periphery of the expansion rod lumen 36 remains in contact with the expansion rod 38 during radial expansion of the flexible elastomeric body 22.

Figure 6A:
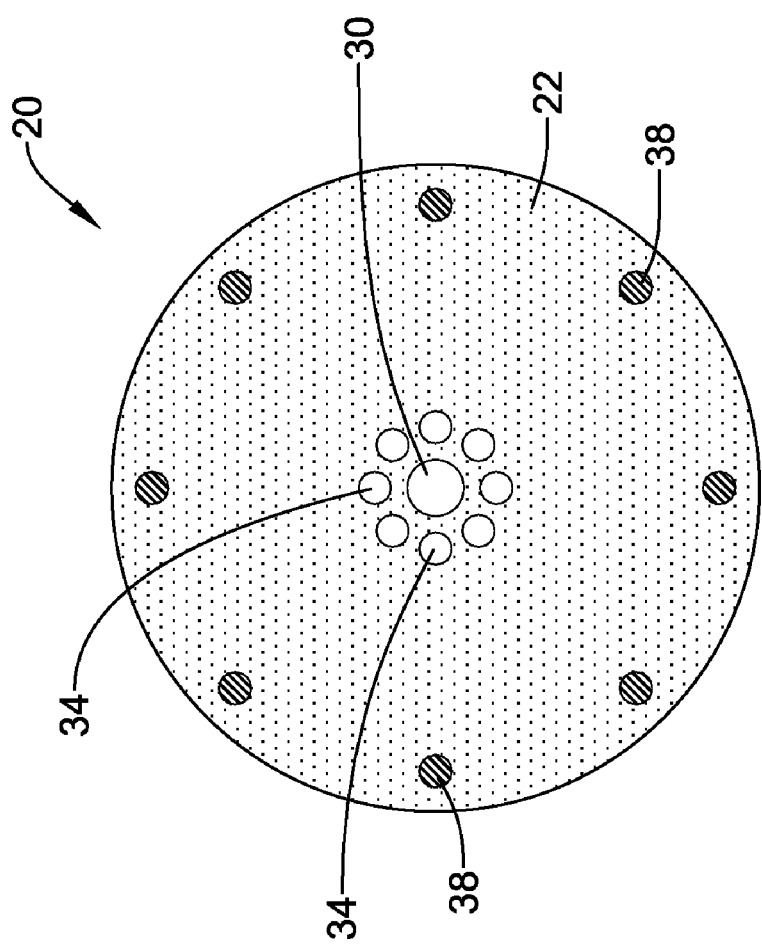
FIGS. 6A and 6B are a transverse cross-sectional view and a longitudinal cross-sectional view, respectively, illustrating the crimping fixture of FIG. 2 with the flexible elastomeric body in a relaxed, unstretched state.
Figure 6B:
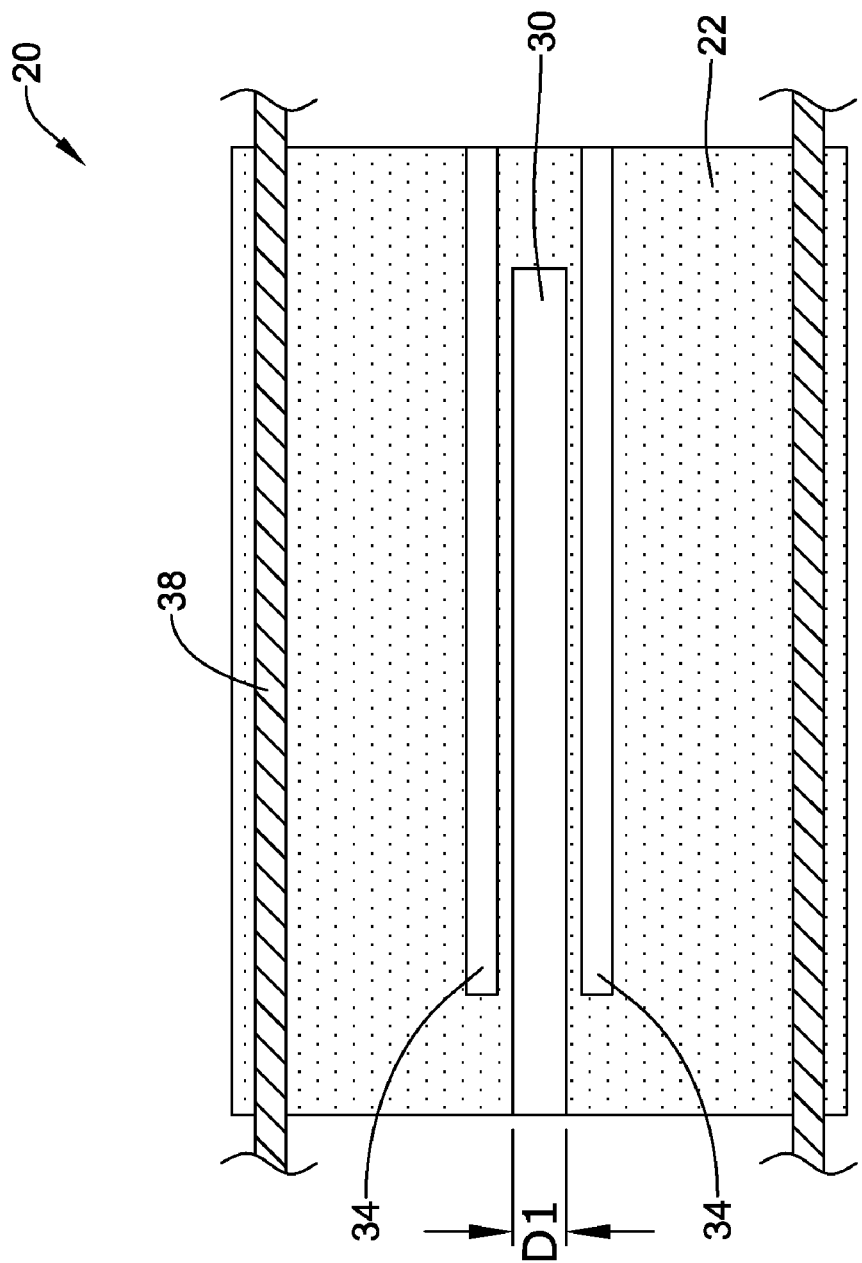

A method of crimping a stent to a balloon of a catheter utilizing the stent crimping fixture 20 will now be described while referring to FIGS. 6A-12B. FIGS. 6A and 6B are a transverse cross-sectional view and a longitudinal cross-sectional view, respectively, illustrating the crimping fixture 20 with the flexible elastomeric body 22 in a relaxed, unstretched state. As shown in FIG. 6B, in the relaxed, unstretched state, the crimping lumen 30 has a first diameter, $D_1$. The first diameter, $D_1$, may be chosen to be smaller than the final, crimped diameter of a stent crimped to a catheter balloon.

Figure 7A:
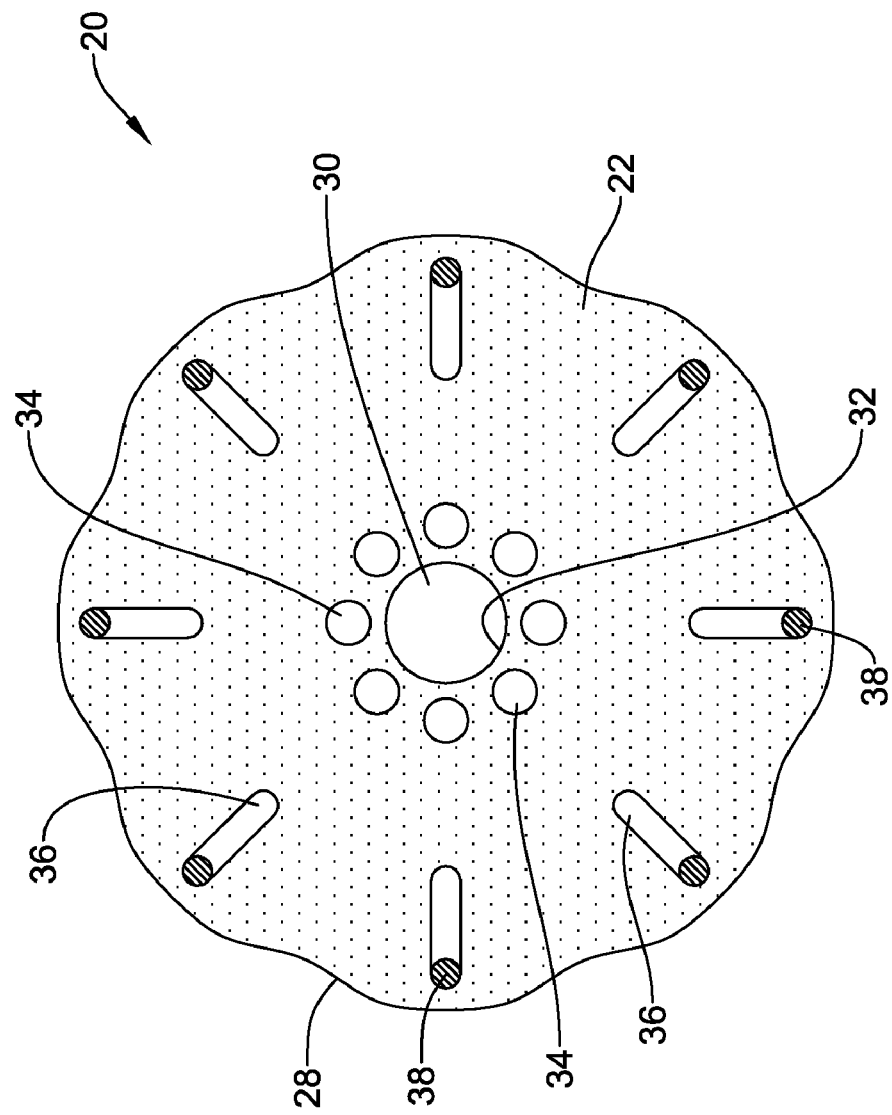
FIGS. 7A and 7B are a transverse cross-sectional view and a longitudinal cross-sectional view, respectively, illustrating the crimping fixture of FIG. 2 with the flexible elastomeric body in an elastically stretched or expanded state.
Figure 7B:
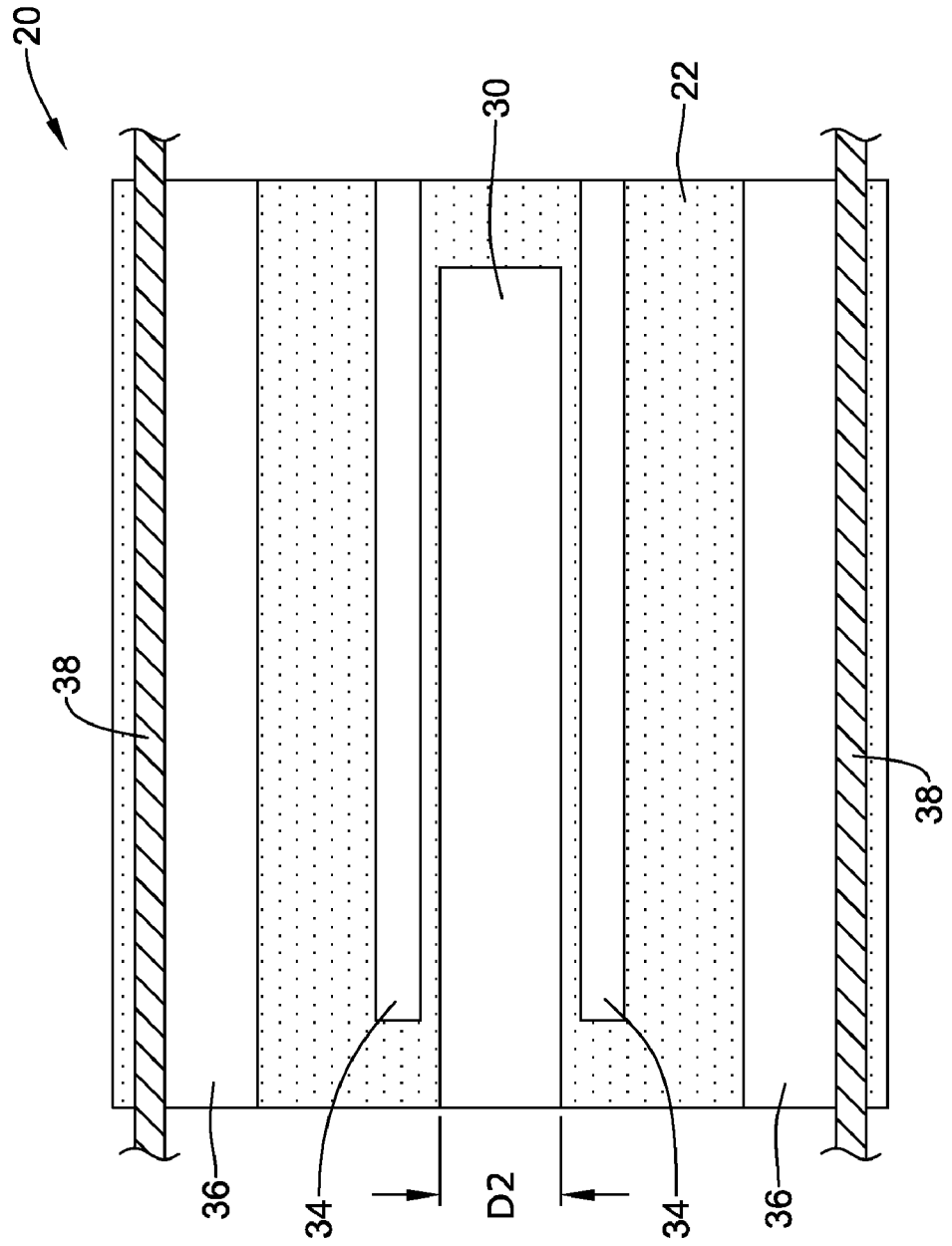

FIGS. 7A and 7B are a transverse cross-sectional view and a longitudinal cross-sectional view, respectively, illustrating the crimping fixture 20 with the flexible elastomeric body 22 in an elastically stretched or expanded state. As shown in FIG. 7B, in the elastically stretched or expanded state, the crimping lumen 30 has a second diameter, $D_2$. The second diameter, $D_2$, is greater than the first diameter, $D_1$. The second diameter, $D_2$, may be greater than the pre-crimped diameter of a stent to be crimped to a catheter balloon. In some embodiments, the second diameter, $D_2$, of the crimping lumen 30 in the elastically stretched or expanded state may be 200% or more, 250% or more, or 300% or more than the first diameter, $D_1$, of the crimping lumen 30 in the relaxed, unstretched state.

During a crimping process, the flexible elastomeric body 22 may be elastically stretched from the relaxed, unstretched state of FIGS. 6A and 6B to the elastically stretched or expanded state of FIGS. 7A and 7B. For example, the cylinders 14 of the crimping machine 10 shown in FIG. 1, or other actuation means, may be actuated to radially expand the arms 40 of the crimping fixture 20. Outward radial actuation of the arms 40 stretches the flexible elastomeric body 22 in order to enlarge the crimping lumen 30 for placement of an pre-crimped stent therein.

Figure 8A:
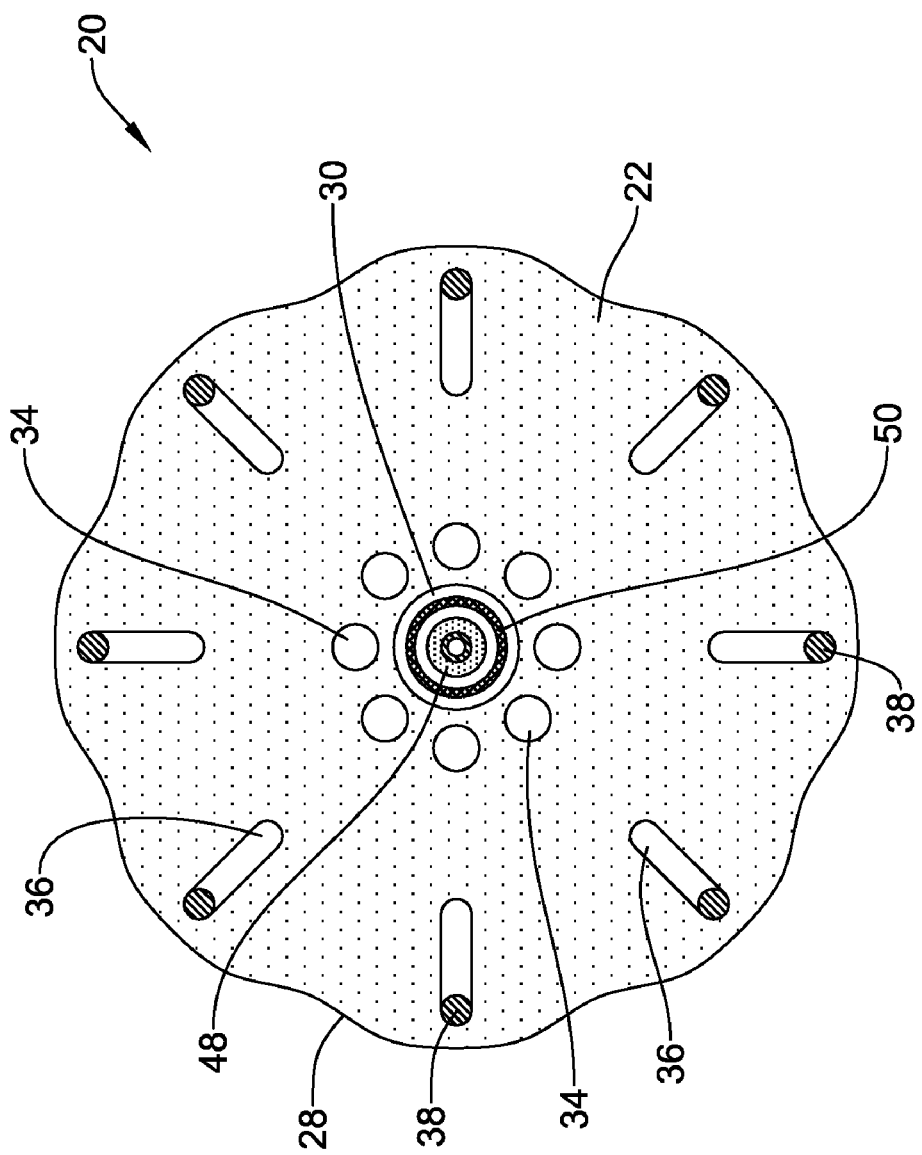
FIGS. 8A and 8B are a transverse cross-sectional view and a longitudinal cross-sectional view, respectively, illustrating a pre-crimped stent disposed on a balloon positioned within the crimping lumen of the flexible elastomeric body of the crimping fixture of FIG. 2 while the flexible elastomeric body is in the elastically stretched or expanded state.
Figure 8B:
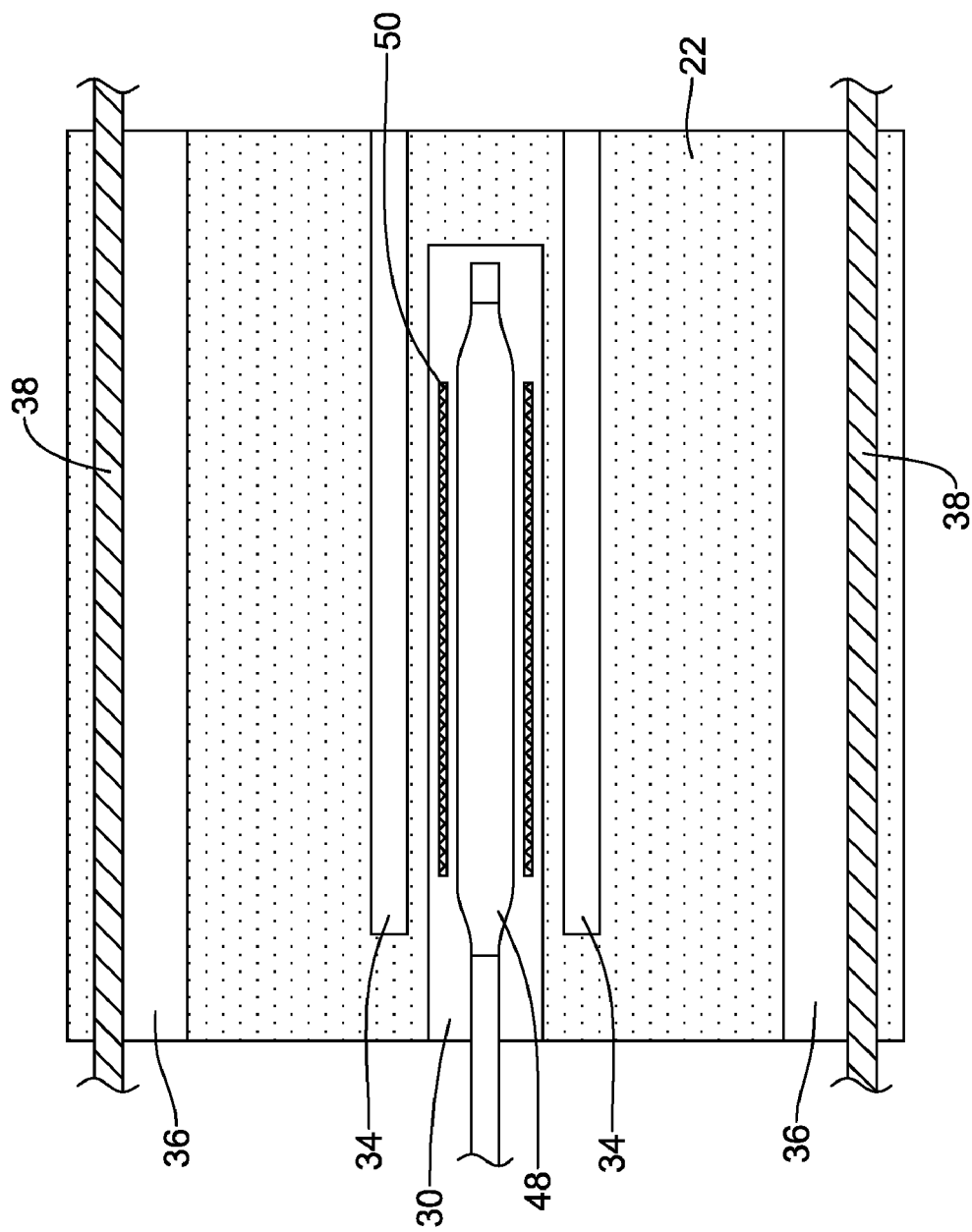

FIGS. 8A and 8B are a transverse cross-sectional view and a longitudinal cross-sectional view, respectively, illustrating a pre-crimped stent 50 disposed around a balloon 48 positioned within the crimping lumen 30 of the flexible elastomeric body 22 while the flexible elastomeric body 22 is in the elastically stretched or expanded state. As shown in FIGS. 8A and 8B, the diameter of the crimping lumen 30 in the elastically stretched or expanded state is greater than the diameter of the pre-crimped stent 50.

After the flexible elastomeric body 22 is elastically stretched such that the crimping lumen 30 is enlarged to the second diameter, $D_2$, a pre-crimped stent 50, having an outside diameter less than the second diameter, $D_2$, of the crimping lumen 30, may be positioned in the crimping lumen 30. Additionally, a portion of a medical device such as a balloon 48 attached to a catheter shaft 52, which may be a folded, deflated or partially deflated (e.g., partially inflated) balloon, of a catheter 46 may be positioned through the pre-crimped stent 50. In some embodiments, the pre-crimped stent 50 may be loaded onto the balloon 48 prior to positioning the stent 50 within the crimping lumen 30. In some embodiments, the pre-crimped stent 50 may be positioned within the crimping lumen 30 such that the pre-crimped stent 50 is completely surrounded by the crimping lumen 30. For example, the entire length of the pre-crimped stent 50 may be positioned between the first end 24 and the second end 26 of the flexible elastomeric body 22.

Figure 9A:
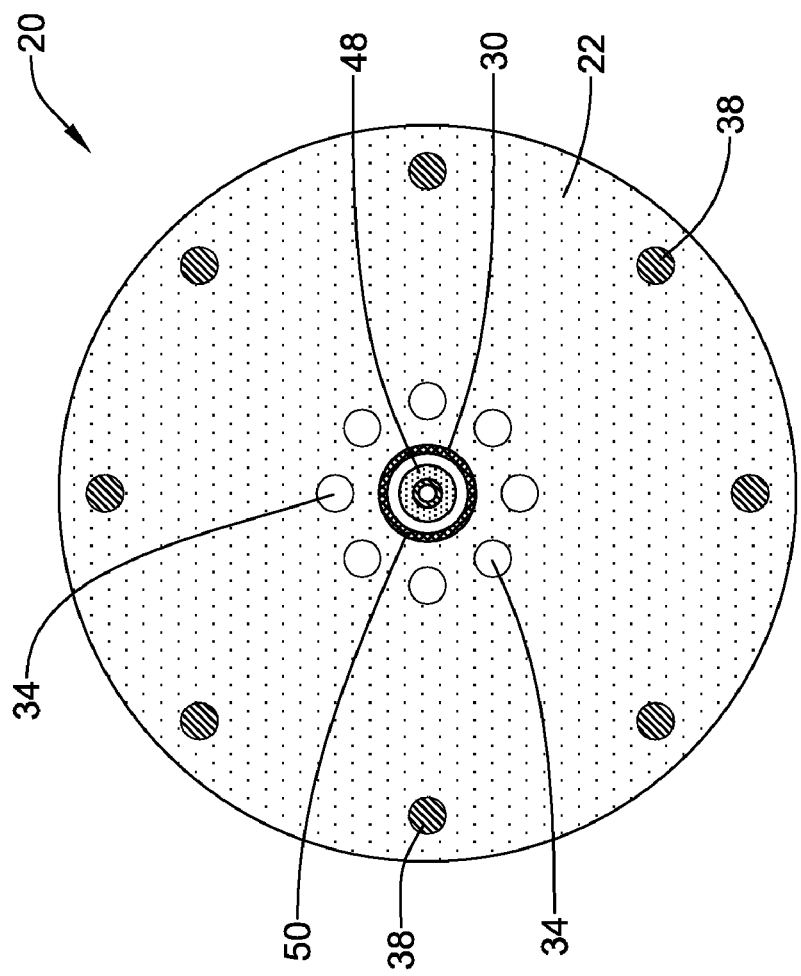
FIGS. 9A and 9B are a transverse cross-sectional view and a longitudinal cross-sectional view, respectively, of the crimping fixture of FIG. 2 with the flexible elastomeric body partially relaxed around the periphery of a pre-crimped stent.
Figure 9B:
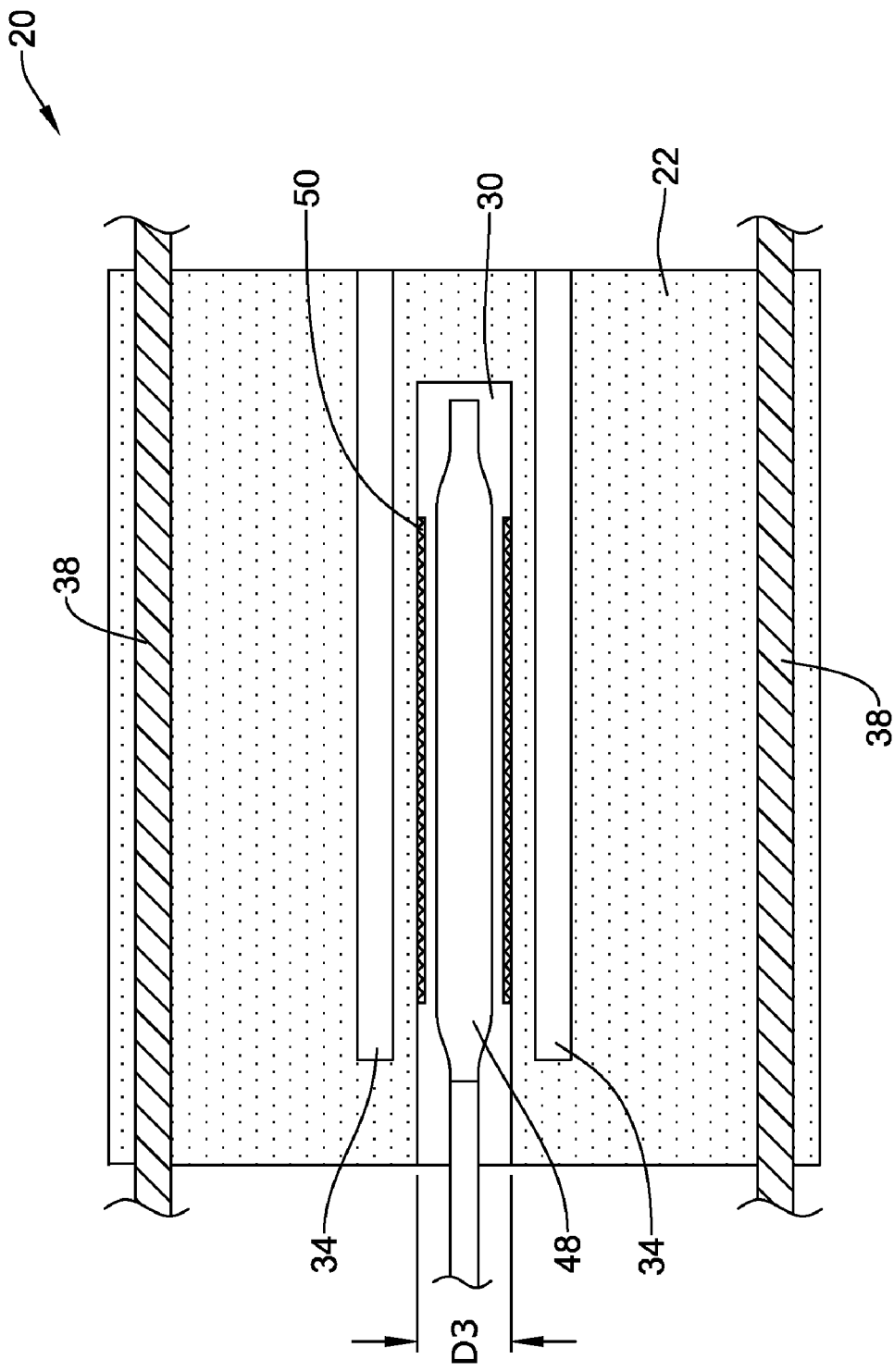

FIGS. 9A and 9B are a transverse cross-sectional view and a longitudinal cross-sectional view, respectively, of the crimping fixture 20 with the flexible elastomeric body 22 partially relaxed such that the inner surface 32 of the crimping lumen 30 conforms around the periphery of the pre-crimped stent 50. Thus the crimping lumen 30 takes the shape of the pre-crimped stent 50. As shown in FIG. 9B, with the flexible elastomeric body 22 partially relaxed around the pre-crimped stent 50, the crimping lumen 30 has a third diameter, $D_3$, substantially equal to the diameter of the stent 50. The third diameter, $D_3$, may be greater than the first diameter, $D_1$, yet less than the second diameter, $D_2$. Thus, with the flexible elastomeric body 22 partially relaxed around the pre-crimped stent 50, the flexible elastomeric body 22 may remain in tension, applying radially compressive forces around the periphery of the stent 50.

Once the pre-crimped stent 50 is positioned in the crimping lumen 30, the flexible elastomeric body 22 may be partially relaxed. For example, the arms 40 of the crimping fixture 20 may be retracted radially inward to allow the flexible elastomeric body to be partially relaxed. However, it is noted that in the partially relaxed state, the flexible elastomeric body 22 remains in tension as the pre-crimped stent 50 prevents the flexible elastomeric body 22 from returning to the relaxed, unstretched state. Thus, as the flexible elastomeric body 22 remains in tension, the inner surface 32 of the crimping lumen 30 tends to conform to the outer surface of the pre-crimped stent 50, applying an inward force on the pre-crimped stent 50.

Figure 10A:
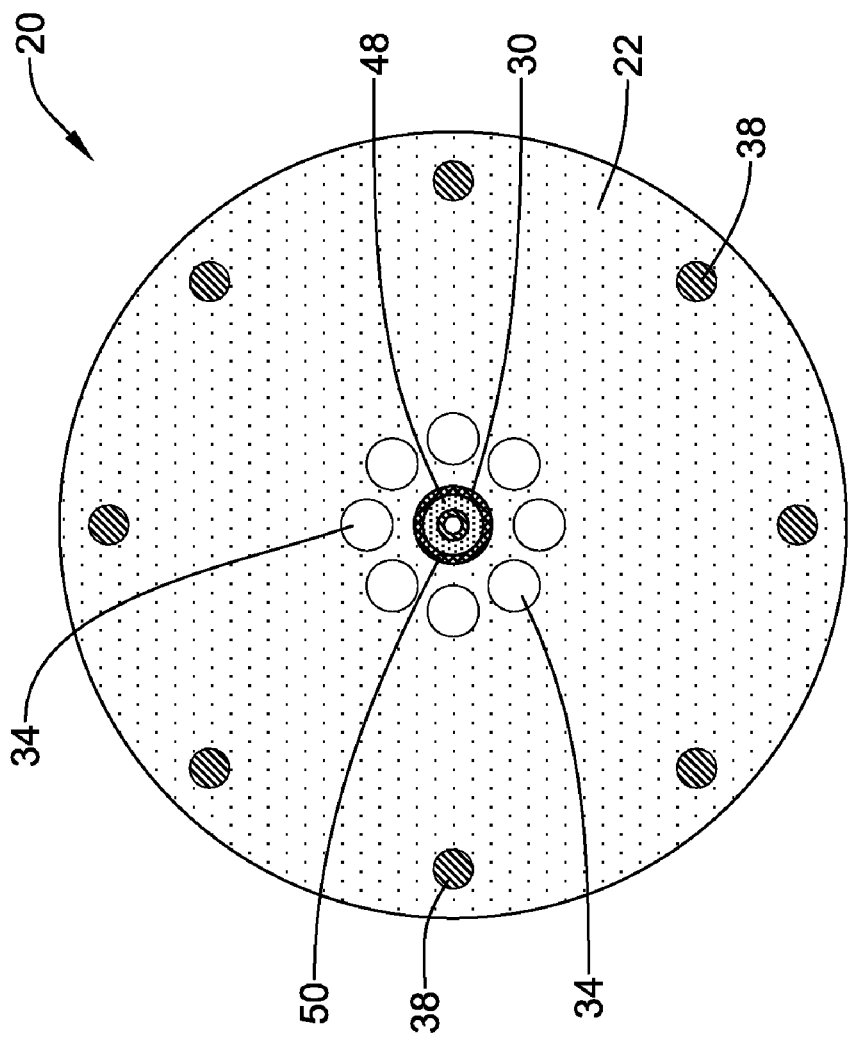
FIGS. 10A and 10B are a transverse cross-sectional view and a longitudinal cross-sectional view, respectively, of the crimping fixture of FIG. 2 as pressurized fluid is introduced into the inflation lumens of the flexible elastomeric body.
Figure 10B:
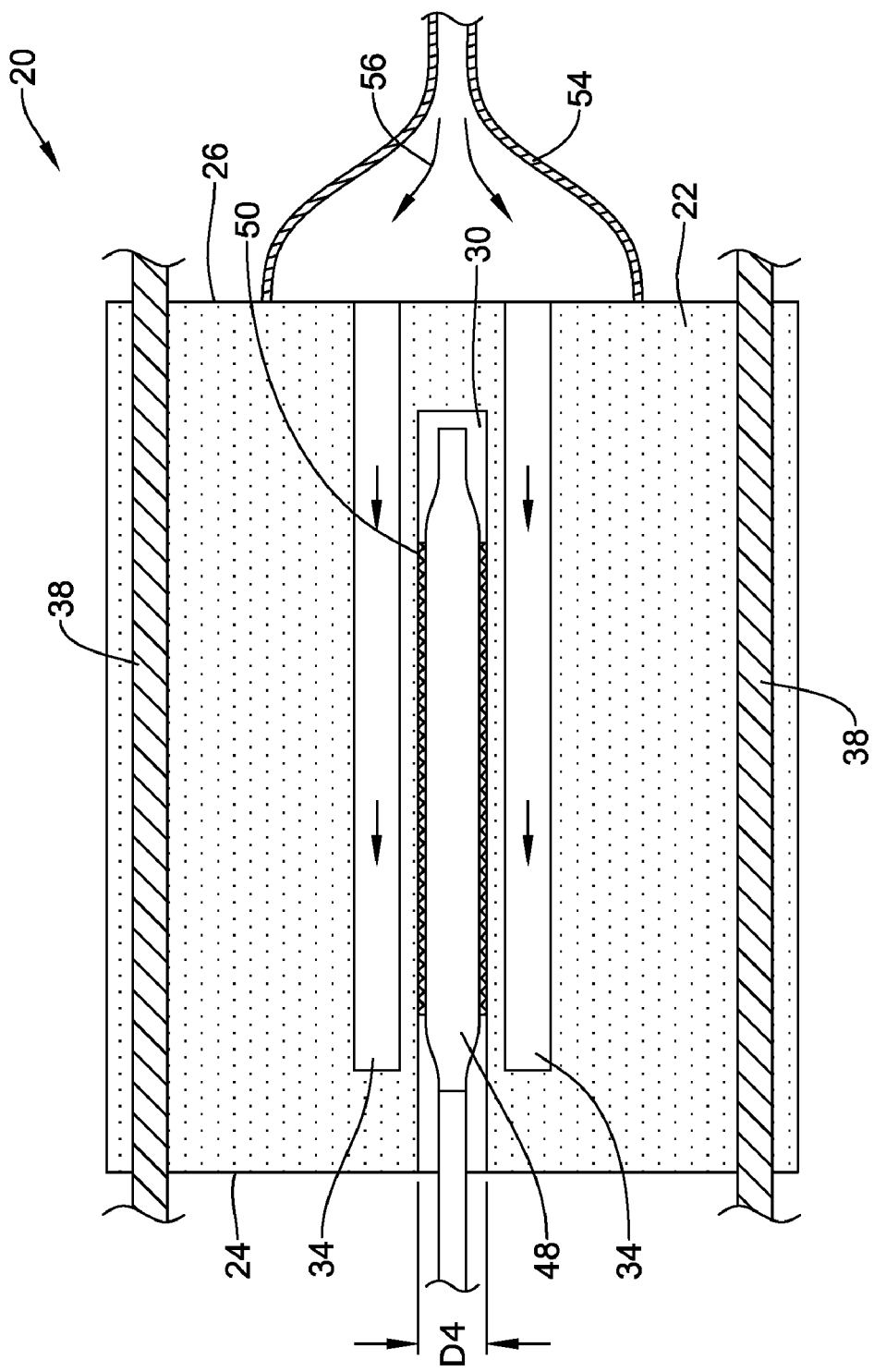

FIGS. 10A and 10B are a transverse cross-sectional view and a longitudinal cross-sectional view, respectively, of the crimping fixture 20 as pressurized fluid 56 is introduced into the inflation lumens 34 through the interior of the nozzle 54 in fluid communication with a source of pressurized fluid. In some embodiments, the pressurized fluid 56 may be a heated fluid, heating the stent 50, balloon 48 and/or other component of the catheter 46 by conduction during the crimping process. A heated crimping cycle may enhance securement of the stent 50 to the balloon 48 by softening the balloon material during crimping.

Once the pre-crimped stent 50 has been positioned in the crimping lumen 30 and the flexible elastomeric body 22 has been partially relaxed around the pre-crimped stent 50 such that the inner surface 32 of the crimping lumen 30 conforms to the outer surface of the pre-crimped stent 50, the inflation lumens 34 may be pressurized with a pressurized fluid 56. For example, the nozzle 54 may be placed in a fluid tight arrangement against the second end 26 of the flexible elastomeric body 22, such that the interior of the nozzle 54, which is in fluid communication with a source of pressurized fluid, directs the pressurized fluid 56 into the inflation lumens 34.

In some embodiments, the inflation lumens 34 may be pressurized to a pressure of about 6 atmospheres (ATM) or greater, about 8 ATM or greater, about 10 ATM or greater, about 12 ATM or greater, about 14 ATM or greater, or 16 ATM or greater. In some embodiments the inflation lumens 34 may be pressurized to a pressure in the range of about 6 ATM to about 16 ATM, in the range of about 8 ATM to about 14 ATM, or in the range of about 10 ATM to about 14 ATM.

Pressurization of the inflation lumens 34 creates an inward force (e.g., radial force=pressure×surface area in contact) acting on the stent 50. The radial compressive force may be transformed into an omni-directional crimping force, normal to the stent 50 at all points of surface contact between the inner surface 32 of the crimping lumen 30 and the outer surface of the stent 50. The inward force created by the pressurization of the inflation lumens 34 causes the stent 50 to be compressed to a smaller outside diameter, thereby crimping the stent 50 to the balloon 48. As the stent 50 is compressed or crimped to a smaller outside diameter, the inner surface 32 of the crimping lumen 30 remains in conforming contact with the outside diameter of the stent 50, as the flexible elastomeric body 22 remains in tension throughout the application of fluid pressurization of the inflation lumens 34. As the inner surface 32 of the crimping lumen 30 remains in conforming contact with the outside diameter of the stent 50, the stent 50 may be subjected to iso-static fluid pressure (e.g., subjected to equal pressure from every side, or contact point).

A pressurized fluid 56 may be continued to be applied until a desired degree of crimping has been attained. For example, in some embodiments a pressure control system may be used to monitor the crimping process. In some instances, the pressure control system will continue to increase pressure until a predetermined pressure, radial force at the interface between the inner surface 32 of the crimping lumen 30 and the stent 50, and/or amount of radial translation (radial compression) of the stent 50 has been achieved. At that point, the pressure control system may maintain the pressure constant for a predetermined amount of time or may cycle the level of pressure through a programmable series of pulses or bursts. A programmable series of pulses or bursts of pressure may provide a dynamic series of force translations to the stent 50. Supplying pressure pulses at a sufficiently high frequency may provide an effect similar to that of subjecting the stent 50 to mechanical or acoustical vibrations.

A pressure control system may also be used to monitor the pressure applied to the inflation lumens 34. By monitoring the pressure applied to the inflation lumens 34, the amount of radial force being applied to the stent 50 may be closely approximated provided that the surface area of the inner surface 32 of the crimping lumen 30 in contact with the stent 50 can be accurately measured or calculated. The radial force applied to the stent 50 may be approximated by the equation:

radial force=pressure×surface area in contact with the stent. In this application, the pressure control system may also serve as a force feedback device.

In some embodiments a pressure control system may be used to individually adjust the inflation pressure of one or more specified inflation lumens 34 to an inflation pressure different from the inflation pressure provided at one or more other inflation lumens 34 of the flexible elastomeric body 22. Providing differential pressure between two or more of the inflation lumens 34 may allow for asymmetric crimping of a stent 50, if desired.

Once the predetermined time of applying pressure and/or the series of pressure pulses is complete, the pressure within the inflation lumens 34 may be reduced and/or the pressurized fluid 56 may be removed from the inflation lumens 34.

An alternative mode of operation during the crimping process could utilize a computerized vision system to provide feedback of the amount of crimping applied to the stent 50. For example, a continual direct visual measurement of the diameter of the crimping lumen 30, and thus the outer diameter of the stent 50, may be used to determine the amount the stent 50 has been crimped. In other embodiments gauges or sensors, such as strain gauges or piezoelectric sensors, molded into the flexible elastomeric body 22 may be used to provide force feedback measurements resulting from the crimping process.

At the completion of the pressurization of the inflation lumens 34, the crimping lumen 30 may have a fourth diameter, $D_4$, less than the third diameter, $D_3$, and greater than the first diameter, $D_1$. Thus, it can be seen that at the conclusion of crimping the stent 50 to a smaller, crimped diameter, the flexible elastomeric body 22, conforming around the periphery of the stent 50, remains in elastic tension. Thus, in some embodiments, the flexible elastomeric body 22 is never placed in compression during the crimping process.

Figure 11A:
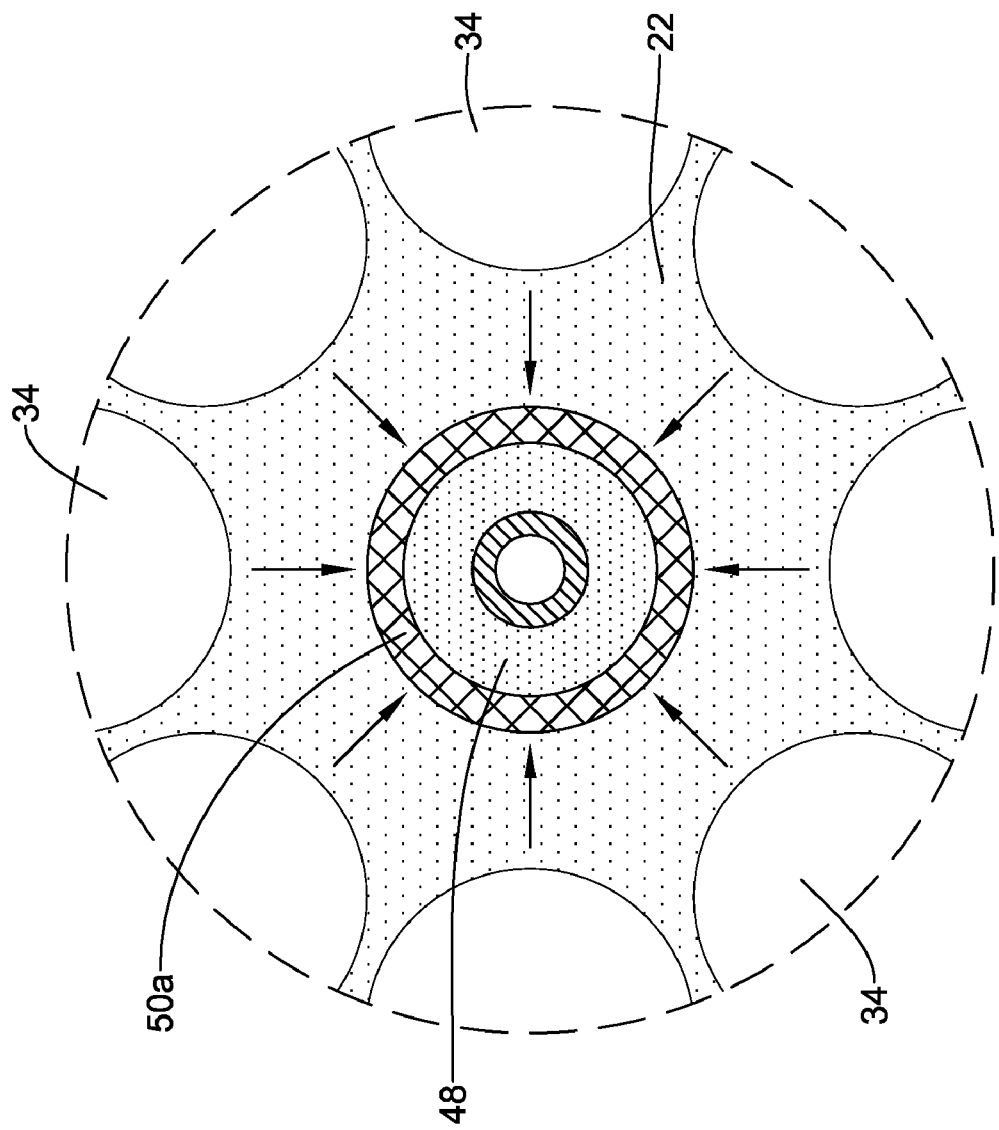
FIG. 11A shows an exemplary circular/symmetrical stent in which the inward crimping forces are projected radially inward around the circumference of the stent.
Figure 11B:
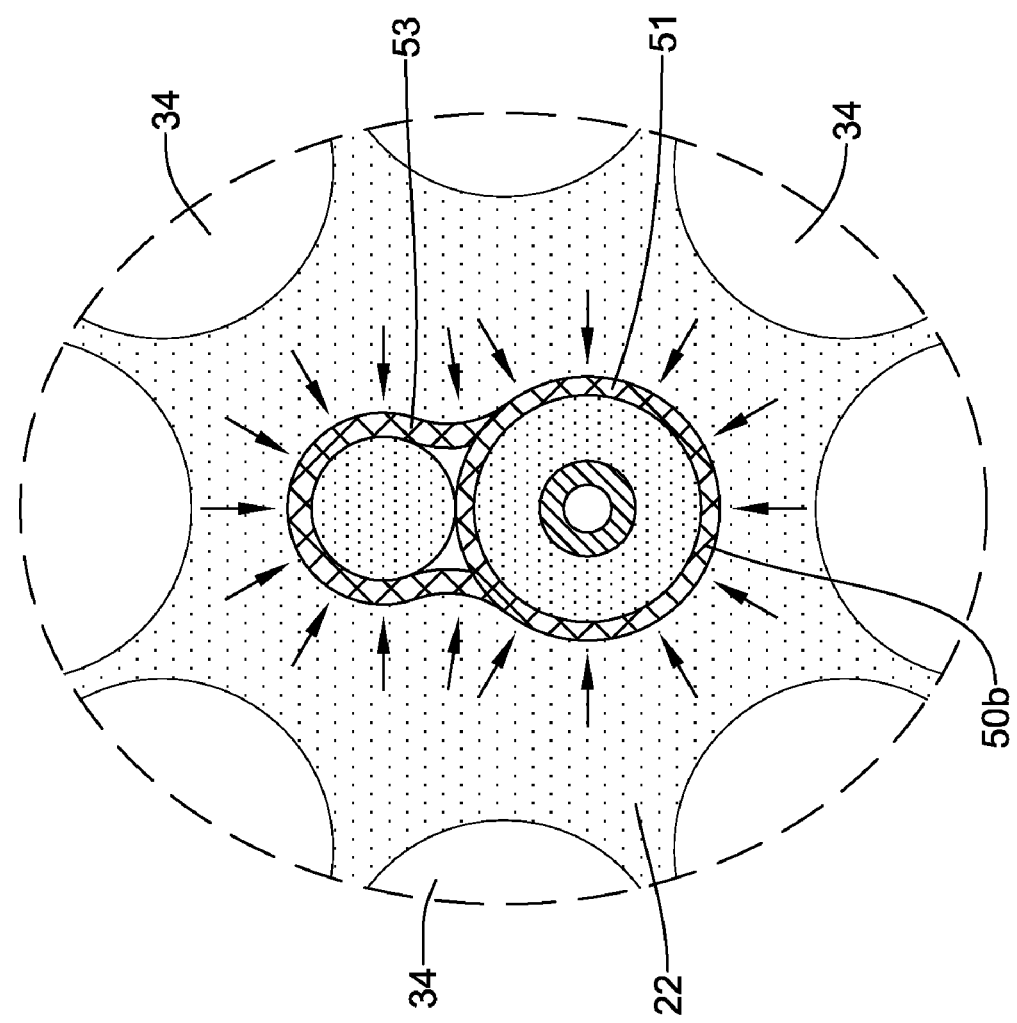
FIG. 11B shows an exemplary non-circular/non-symmetrical stent in which the inward crimping forces are projected inward around the periphery of the stent.

As shown in FIGS. 11A and 11B, pressurization of the inflation lumens 34 creates an inward force normal at all points of contact between the inner surface 32 of the crimping lumen 30 and the outer surface of the stent 50. In other embodiments, radially inward movement of the expansion rods 38 could provide a radially inward crimping force on the flexible elastomeric body 22.

FIG. 11A shows a typical circular/symmetrical stent 50a in which the inward crimping forces are projected radially inward around the circumference of the stent 50a. The inner surface 32 of the crimping lumen 30 is shown in conformal contact with the outer surface of the stent 50a along the entire periphery of the stent 50a, or substantially the entire periphery of the stent 50a. Thus, iso-static fluid pressure from the inflation lumens 34 is transformed into an omni-directional crimping force (shown by arrows), normal to the stent 50a at all points of surface contact between the inner surface 32 of the crimping lumen 30 and the outer surface of the stent 50a.

FIG. 11B shows an exemplary non-circular/non-symmetrical stent 50b, illustrated as a bifurcated stent. The stent 50b includes a main portion 51 and a side branch portion 53. As shown in FIG. 11B, the inward crimping forces are projected inward around the periphery of the stent 50b. The inner surface 32 of the crimping lumen 30 is shown in conformal contact with the outer surface of the stent 50b along the entire periphery, or substantially the entire periphery, of the stent 50b. Thus, iso-static fluid pressure from the inflation lumens 34 is transformed into an omni-directional crimping force (shown by arrows), normal to the stent 50b at all points of surface contact between the inner surface 32 of the crimping lumen 30 and the outer surface of the stent 50b.

Figure 12A:
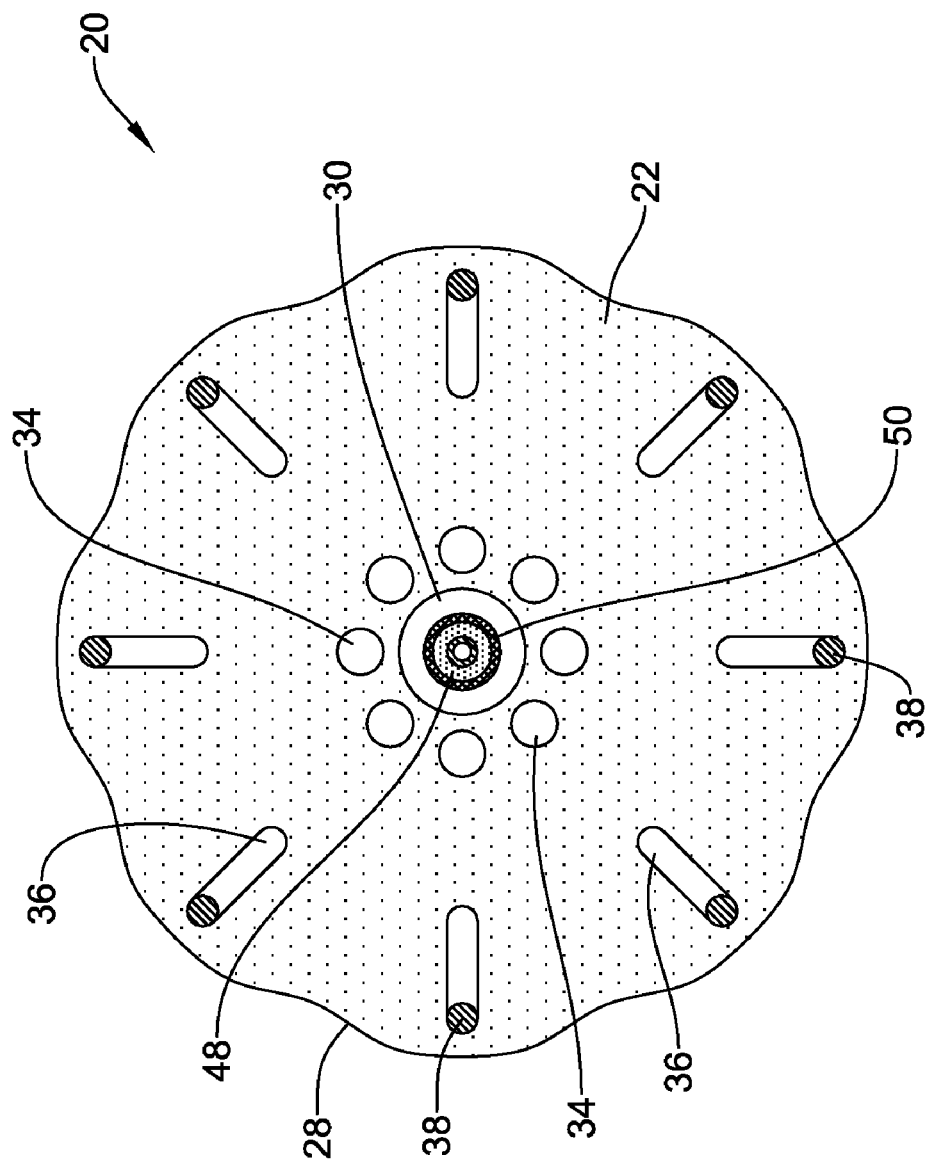
FIGS. 12A and 12B are a transverse cross-sectional view and a longitudinal cross-sectional view, respectively, of the crimping fixture of FIG. 2 after a stent has been crimped to a balloon and the flexible elastomeric body has been radially expanded in order to remove the catheter with crimped stent from the crimping lumen of the flexible elastomeric body.
Figure 12B:
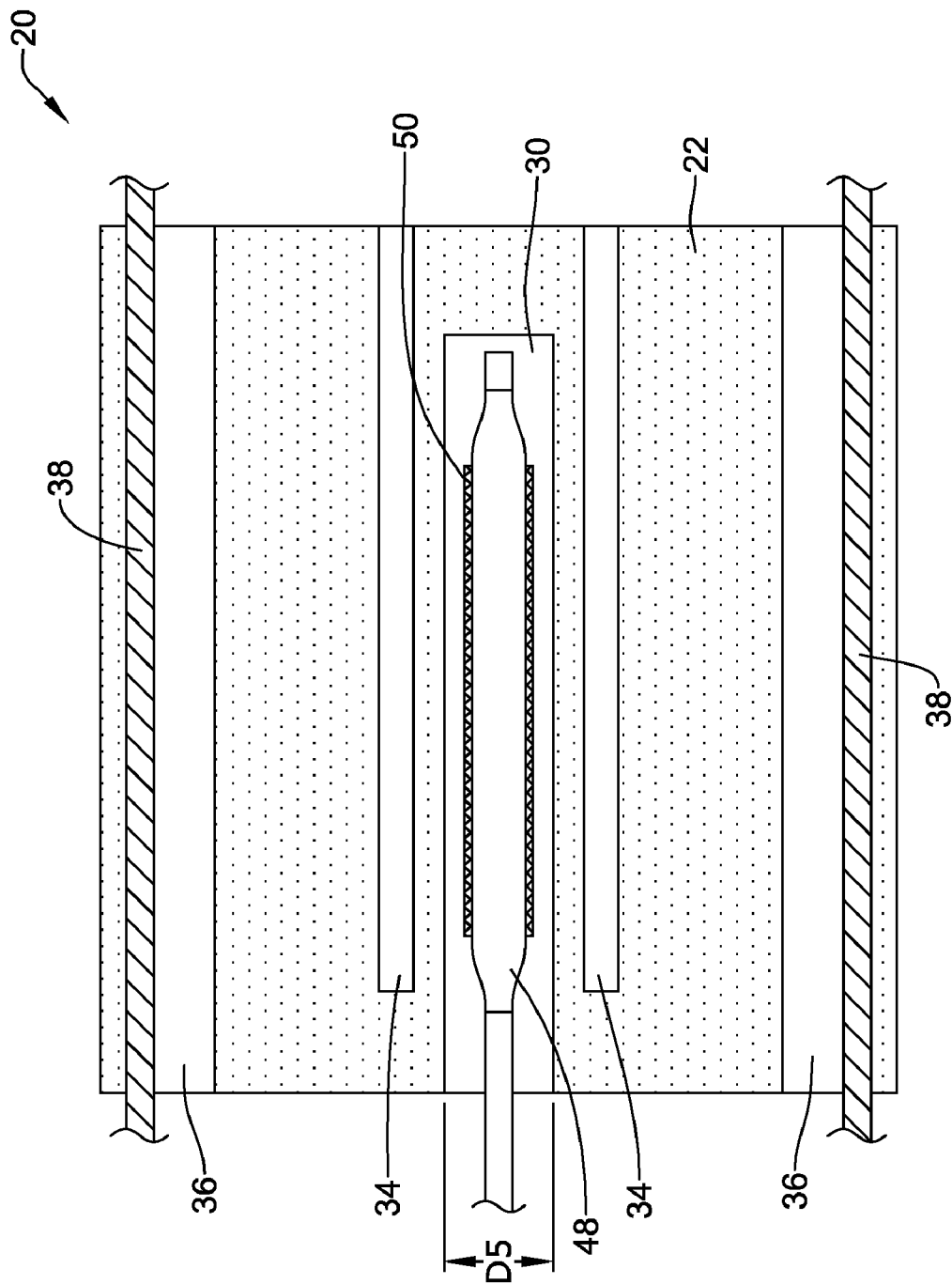

FIGS. 12A and 12B are a transverse cross-sectional view and a longitudinal cross-sectional view, respectively, of the crimping fixture 20 after the stent 50 has been crimped to the balloon 48 and the flexible elastomeric body 22 has been radially expanded in order to remove the catheter 46 with crimped stent 50 from the crimping lumen 30. By once again elastically stretching or expanding the flexible elastomeric body 22, the crimping lumen 30 is enlarged such that the inner surface 32 of the crimping lumen 30 is dissociated or disconnected from the outer surface of the stent 50.

Once the stent 50 has been crimped to the balloon 48 of the catheter 46, the flexible elastomeric body 22 may again be elastically stretched. For example, the cylinders 14 of the crimping machine 10 shown in FIG. 1, or other actuation means, may be actuated to radially expand the arms 40 of the crimping fixture 20. Outward radial actuation of the arms 40 stretches the flexible elastomeric body 22 in order to enlarge the crimping lumen 30 for removal of a crimped stent 50 and/or the placement of another pre-crimped stent 50 therein. In some embodiments, the flexible elastomeric body 22 may be elastically stretched such that the diameter of the crimping lumen 30 is larger than the diameter of the crimped stent 50. For example, in some embodiments the crimping lumen 30 may be stretched to a fifth diameter, $D_5$, which in some embodiments may be equal to or substantially equal to the diameter, $D_2$. Thus, the crimping lumen 30 of the flexible elastomeric body 22 may be elastically stretched for receiving another pre-crimped stent 50.

In some embodiments, the stent 50 may be coated with a drug-eluting coating prior to and/or subsequent the crimping process. In instances where the stent 50 is coated with a drug-eluting coating prior to the crimping process, it may be understood that the flexible elastomeric body 22 may not appreciably harm the drug-eluting coating during the crimping process. For example, the flexible elastomeric body 22 may not leave any discernable tool marks, witness lines, etc. on the surface of the stent 50 and/or on the surface of the drug-eluting coating, which may be evident with other crimping processes.

It is noted that in some embodiments, it may be possible to inflate the inflation lumens 34 with a pressurized fluid 56 to crimp a stent 50 with the flexible elastomeric body 22 in the elastically stretched state shown in FIGS. 8A and 8B. Thus, in some embodiments it may be possible to forego the step of partially relaxing the flexible elastomeric body 22 around the pre-crimped stent 50, as shown in FIGS. 9A and 9B, prior to crimping a stent 50 to a balloon 48. Thus, the arms 40 may mechanically hold the flexible elastomeric body 22 in an elastically stretched state throughout the crimping process. Therefore, a stent 50 may be crimped to a balloon 48 by pressurizing the inflation lumens 34 with the flexible elastomeric body 22 in the elastically stretched state. The crimped stent 50 may be removed from the crimping lumen 30 upon depressurizing the inflation lumens 34 with the flexible elastomeric body 22 in the elastically stretched state, and the crimping lumen 30 may be ready for placement of another pre-crimped stent 50 therein.

Other illustrative flexible elastomeric bodies, similar to the flexible elastomeric body 22, are shown in FIGS. 13-19. FIGS. 13-19 are transverse cross-sectional views of the flexible elastomeric bodies, showing the various lumens and other components of the flexible elastomeric bodies. Similar to the flexible elastomeric body 22, each of these illustrative flexible elastomeric bodies may be formed of a suitable elastomeric material, including, but not necessarily limited to, those materials listed above with regard to the flexible elastomeric body 22.

Figure 13:
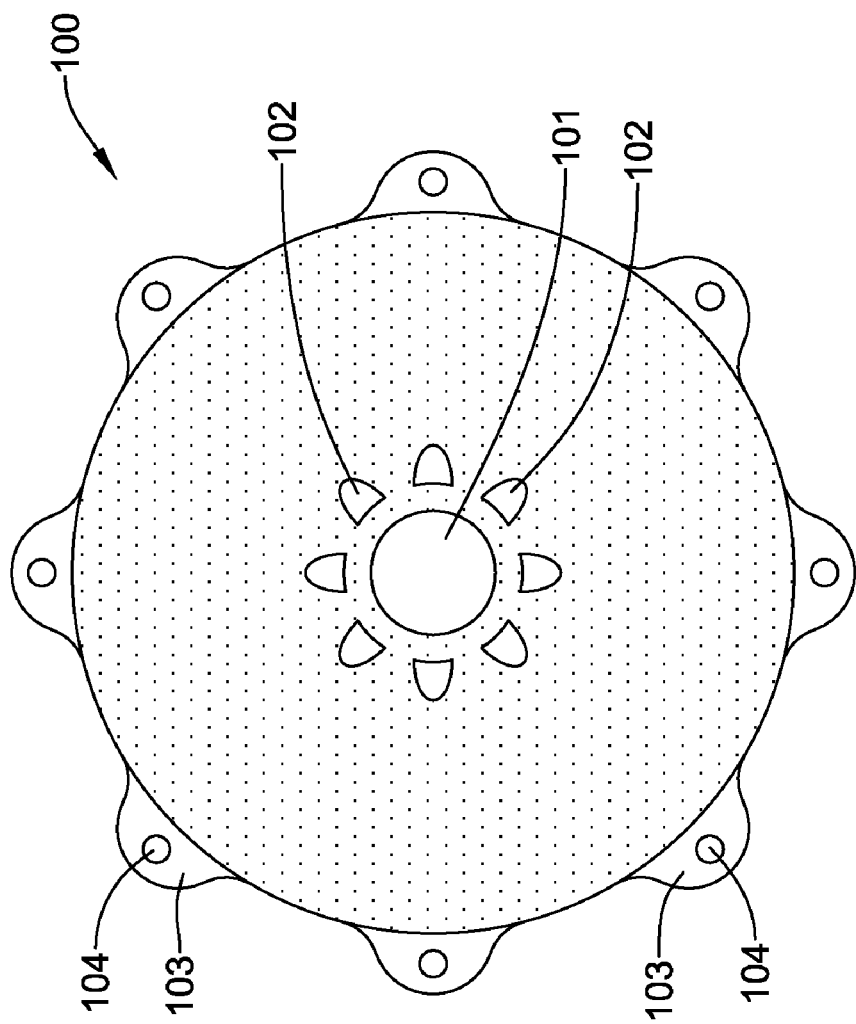
FIGS. 13-19 are transverse cross-sectional views of several alternative flexible elastomeric bodies, showing the various lumens and other components of the flexible elastomeric bodies.

FIG. 13 shows a flexible elastomeric body 100. The flexible elastomeric body 100 includes a central crimping lumen 101 longitudinally extending through at least a portion of the length of the flexible elastomeric body 100. A plurality of inflation lumens 102 are positioned around the crimping lumen 101. For example, the inflation lumens 102 may be arranged in a radial array around the crimping lumen 101. The inflation lumens 102 may be non-circular in shape. For example, the inflation lumens 102 may be wedge-shaped, or pedal-shaped, having an apex directed radially away from the crimping lumen 101.

The flexible elastomeric body 100 may also include a plurality of loops 103 having openings 104 extending from the outer surface 105 of the flexible elastomeric body 100. The loops 103 may be used to elastically stretch the flexible elastomeric body 100 during a crimping procedure. Thus, during a crimping process, the loops 103 may be attached to an actuation device, which is radially actuatable. The loops 103 may be attached to the flexible elastomeric body 100 during a molding process, or other suitable process. In some embodiments, the loops 103 may be bonded to the flexible elastomeric body 100, such as with an adhesive. In other embodiments, the loops 103 may be molded or extruded with the flexible elastomeric body 100. Thus, in some embodiments the loops 103 and the flexible elastomeric body 100 may be a monolithic structure formed of the same material.

Figure 14:
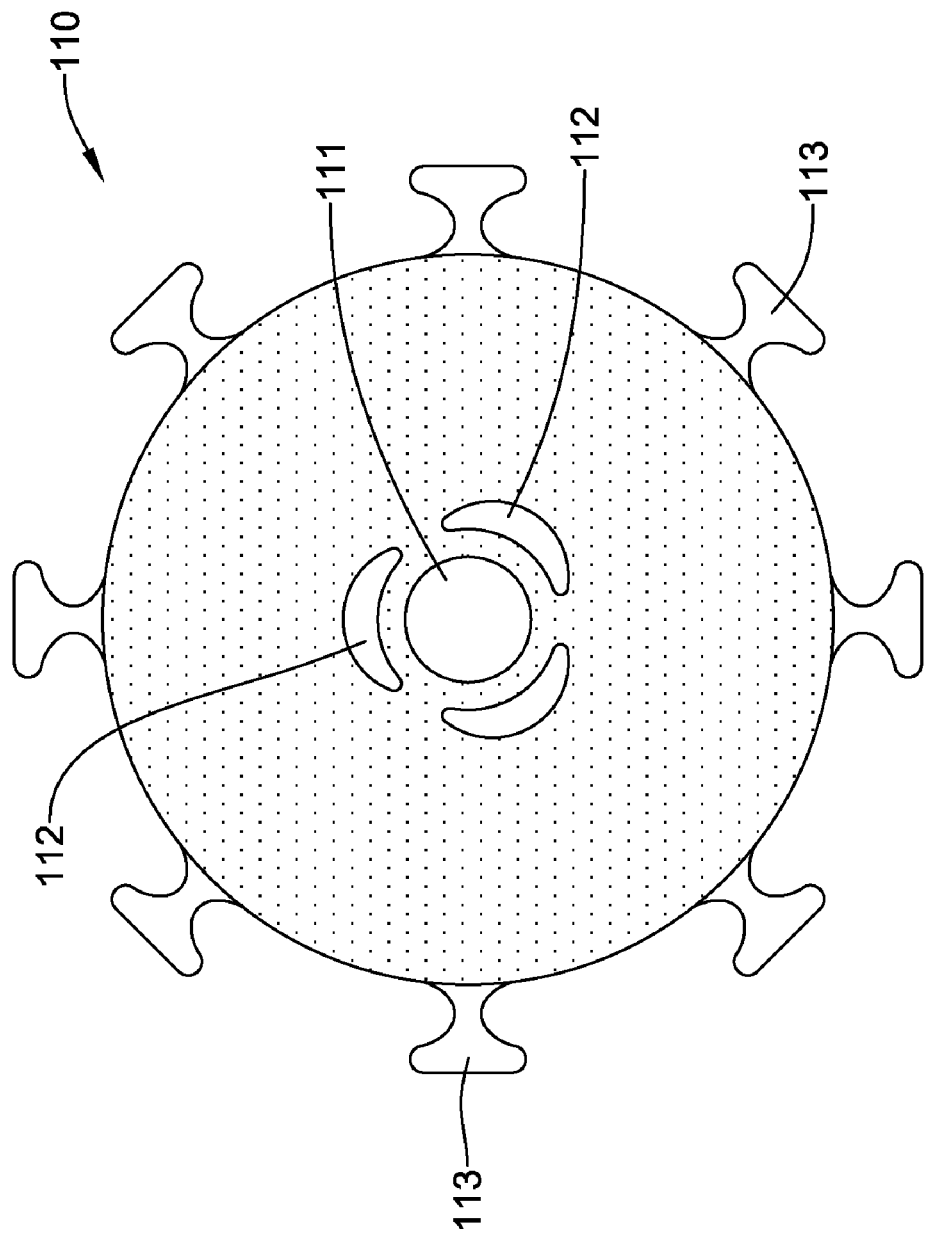

FIG. 14 shows a flexible elastomeric body 110. The flexible elastomeric body 110 includes a central crimping lumen 111 longitudinally extending through at least a portion of the length of the flexible elastomeric body 110. A plurality of inflation lumens 112 are positioned around the crimping lumen 111. For example, the inflation lumens 112 may be arranged in a radial array around the crimping lumen 111. The inflation lumens 112 may be non-circular in shape. For example, the inflation lumens 112 may be kidney shaped or arcuate shaped having a concave side adjacent the crimping lumen 111.

The flexible elastomeric body 110 may also include a plurality of projections 113 extending from the outer surface 115 of the flexible elastomeric body 110. The projections 113 may be used to elastically stretch the flexible elastomeric body 110 during a crimping procedure. Thus, during a crimping process, the projections 113 may be attached to an actuation device, which is radially actuatable. The projections 113 may be attached to the flexible elastomeric body 110 during a molding process, or other suitable process. In some embodiments, the projections 113 may be bonded to the flexible elastomeric body 110, such as with an adhesive. In other embodiments, the projections 113 may be molded or extruded with the flexible elastomeric body 110. Thus, in some embodiments the projections 113 and the flexible elastomeric body 110 may be a monolithic structure formed of the same material.

Figure 15:
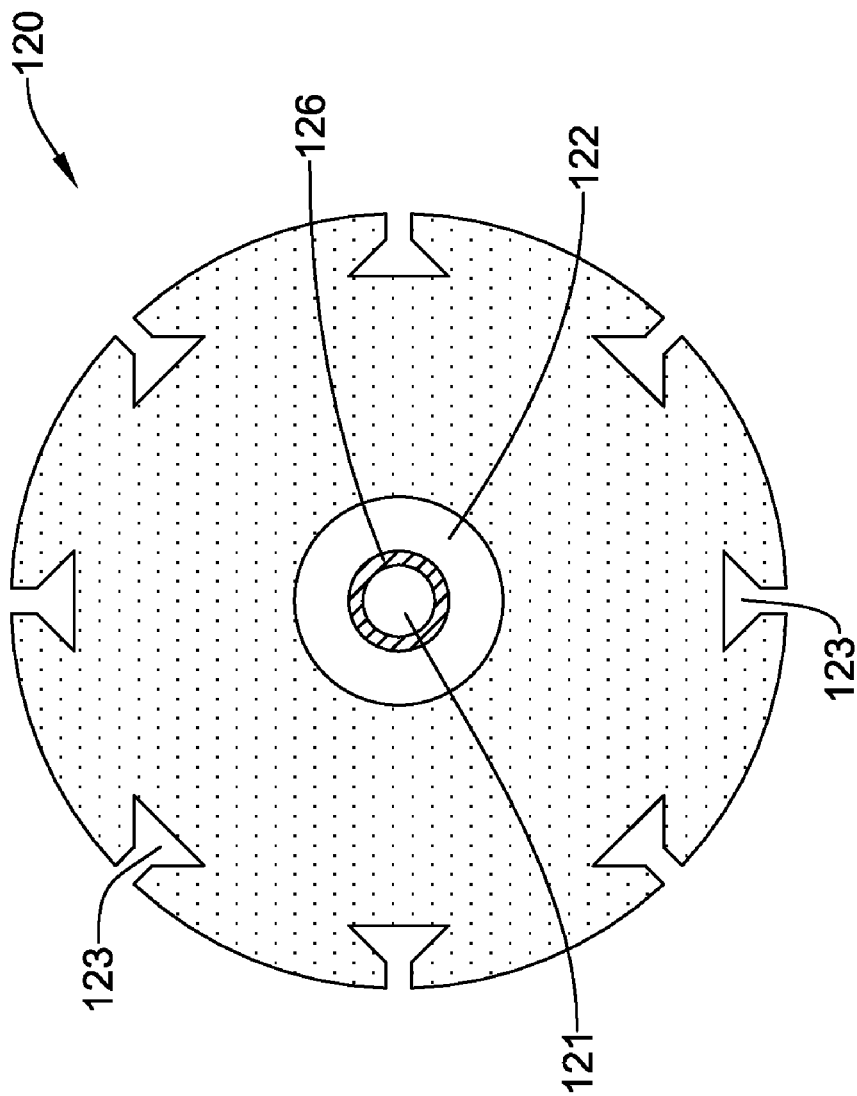

FIG. 15 shows a flexible elastomeric body 120. The flexible elastomeric body 120 includes a central crimping lumen 121 longitudinally extending through at least a portion of the length of the flexible elastomeric body 120. An annular inflation lumen 122 is positioned circumferentially around the crimping lumen 121. An annular ring 126 of flexible elastomeric material of the flexible elastomeric body 120 may be located between the crimping lumen 121 and the inflation lumen 122.

The flexible elastomeric body 120 may also include a plurality of recesses 123 extending from the outer surface 125 radially into the flexible elastomeric body 120. The recesses 123 may be used to elastically stretch the flexible elastomeric body 120 during a crimping procedure. Thus, during a crimping process, the recesses 123 may receive an actuation device, which is radially actuatable. The recesses 123 may be formed in the flexible elastomeric body 120 during a molding process, extrusion process, or other suitable process.

Figure 16:
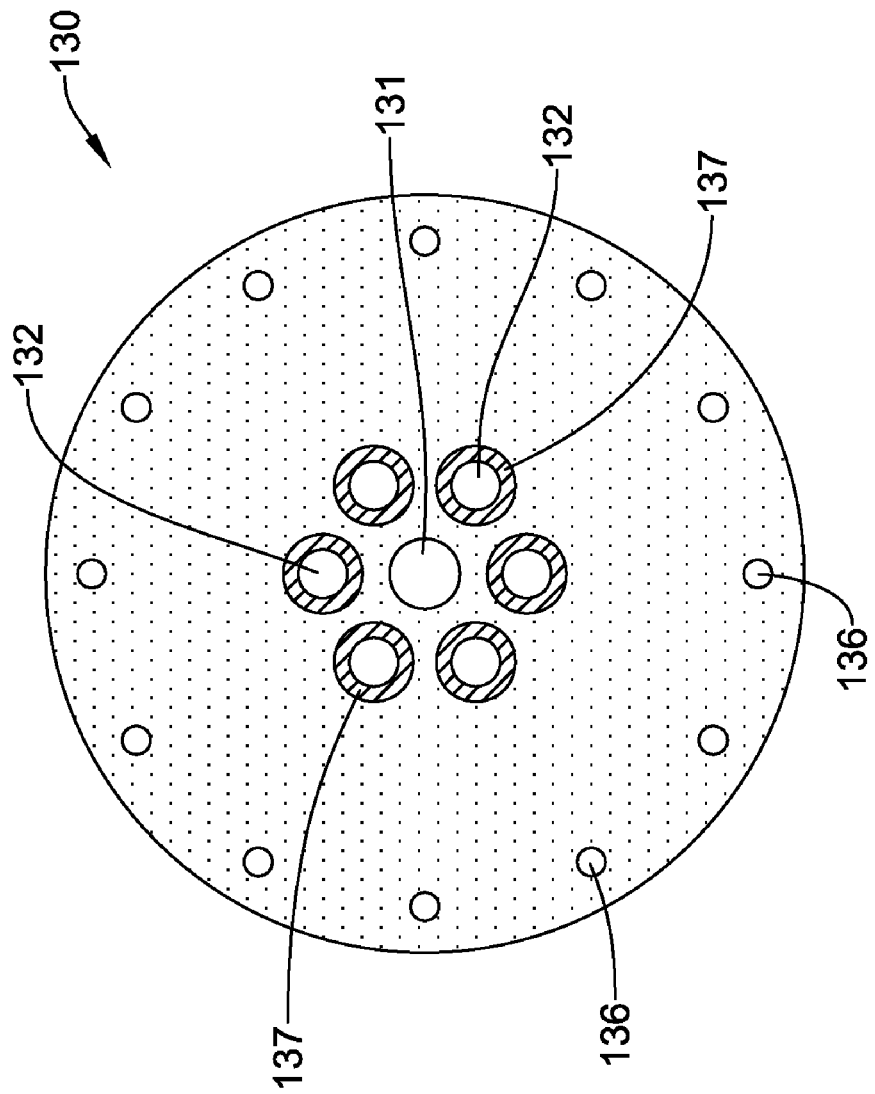

FIG. 16 shows a flexible elastomeric body 130. The flexible elastomeric body 130 includes a central crimping lumen 131 longitudinally extending through at least a portion of the length of the flexible elastomeric body 130. A plurality of inflation lumens 132 are positioned around the crimping lumen 131. For example, the inflation lumens 132 may be arranged in a radial array around the crimping lumen 131. One or more rigid members 137, such as metallic tubes and/or rods, may be located within one or more of the inflation lumens 132. The rigid members 137 may facilitate crimping a stent onto a balloon by adding rigidity to the flexible elastomeric body 130 as the crimping lumen 131 is in conforming contact around the stent. In some embodiments, the rigid members 137 may include transverse openings in the annular wall of the rigid members 137 and/or the annular wall of the rigid members 137 may be permeable in order that an inflation fluid introduced into the lumen of the rigid members 137 may expand the inflation lumens 132 around the rigid members 137.

The flexible elastomeric body 130 may also include a plurality of expansion rod lumens 136, similar to the expansion rod lumens 36 of the flexible elastomeric body 22. The expansion rod lumens 136 may be radially arranged around the flexible elastomeric body 130 in order to facilitate elastically stretching the flexible elastomeric body 130 radially outward.

Figure 17:
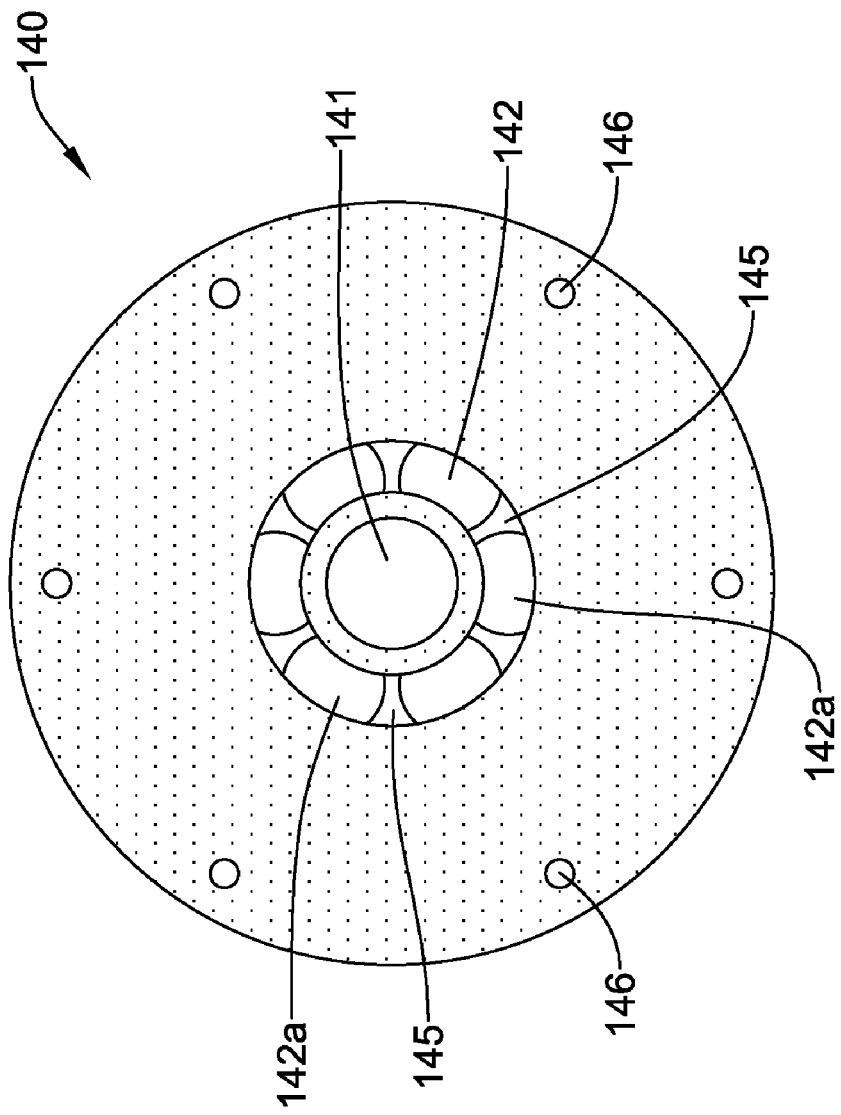

FIG. 17 shows a flexible elastomeric body 140. The flexible elastomeric body 140 includes a central crimping lumen 141 longitudinally extending through at least a portion of the length of the flexible elastomeric body 140. An inflation lumen 142 including a plurality of inflation chambers 142a is positioned circumferentially around the crimping lumen 141. The plurality of inflation chambers 142a of the inflation lumen 142 may be in fluid communication with one another, with a plurality of tendrils 145 spanning across the inflation lumen 142 at several locations. Thus a pressurized fluid may be equalized throughout each of the inflation chambers 142a of the inflation lumen 142 during a crimping process.

The flexible elastomeric body 140 may also include a plurality of expansion rod lumens 146, similar to the expansion rod lumens 36 of the flexible elastomeric body 22. The expansion rod lumens 146 may be radially arranged around the flexible elastomeric body 140 in order to facilitate elastically stretching the flexible elastomeric body 140 radially outward.

Figure 18:
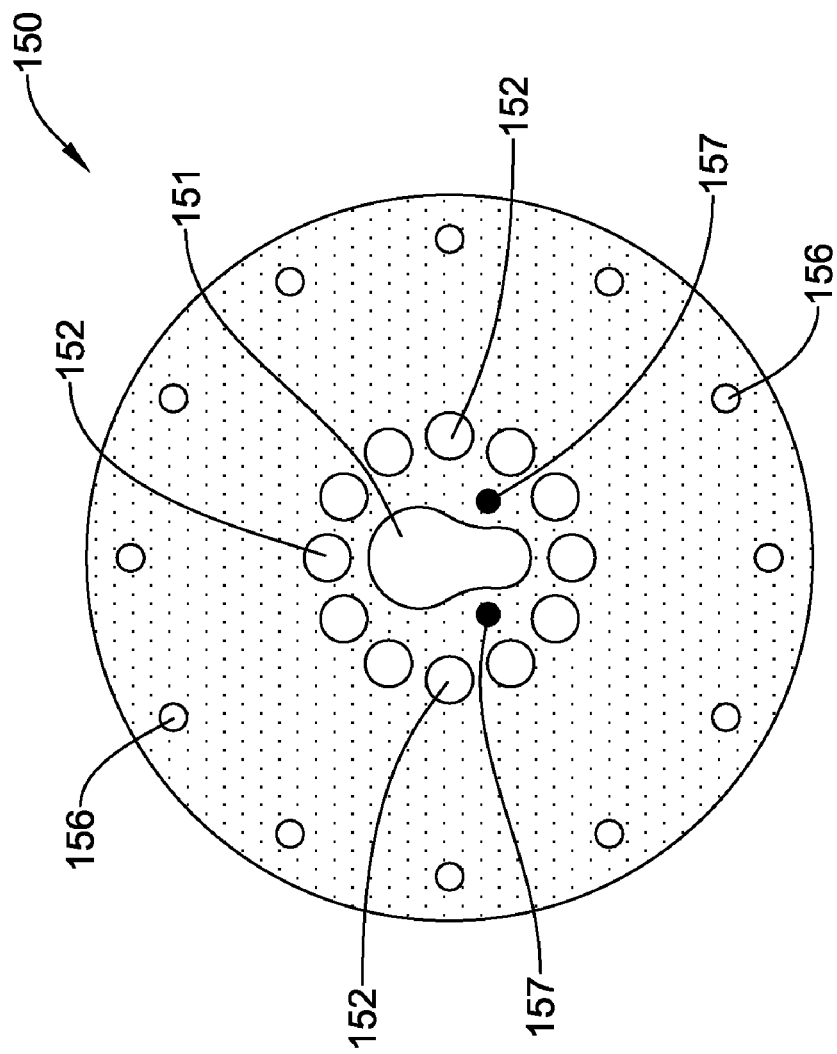

FIG. 18 shows a flexible elastomeric body 150. The flexible elastomeric body 150 includes a central crimping lumen 151 longitudinally extending through at least a portion of the length of the flexible elastomeric body 150. The crimping lumen 151 may be non-circular in shape in order to more precisely trace the periphery of a non-circular/non-symmetrical stent. For example, the crimping lumen 151 may be keyhole shaped, having a larger circular portion adjacent a smaller circular portion. Such a shape may be found to more closely approximate the profile of a bifurcated stent.

A plurality of inflation lumens 152 may be positioned around the crimping lumen 151. For example, the inflation lumens 152 may be arranged in a radial array around the crimping lumen 151. In addition to the inflation lumens 152, one or more rigid members 157, such as metallic tubes and/or rods, may longitudinally extend along the flexible elastomeric body 150. The rigid members 157 may be formed with the flexible elastomeric body 150 during an extrusion or molding process, for example, or the rigid members 157 may be placed in the flexible elastomeric body 150 subsequent to forming the flexible elastomeric body 150. The rigid members 157 may facilitate crimping a stent onto a balloon by adding rigidity to the flexible elastomeric body 150 as the crimping lumen 151 is in conforming contact around the stent. For example, the rigid members 157 may be located at the recessed regions of the key-hole shaped crimping lumen 151 to provide additional inward force at this region around the periphery of a stent.

The flexible elastomeric body 150 may also include a plurality of expansion rod lumens 156, similar to the expansion rod lumens 36 of the flexible elastomeric body 22. The expansion rod lumens 156 may be radially arranged around the flexible elastomeric body 150 in order to facilitate elastically stretching the flexible elastomeric body 150 radially outward.

Figure 19:
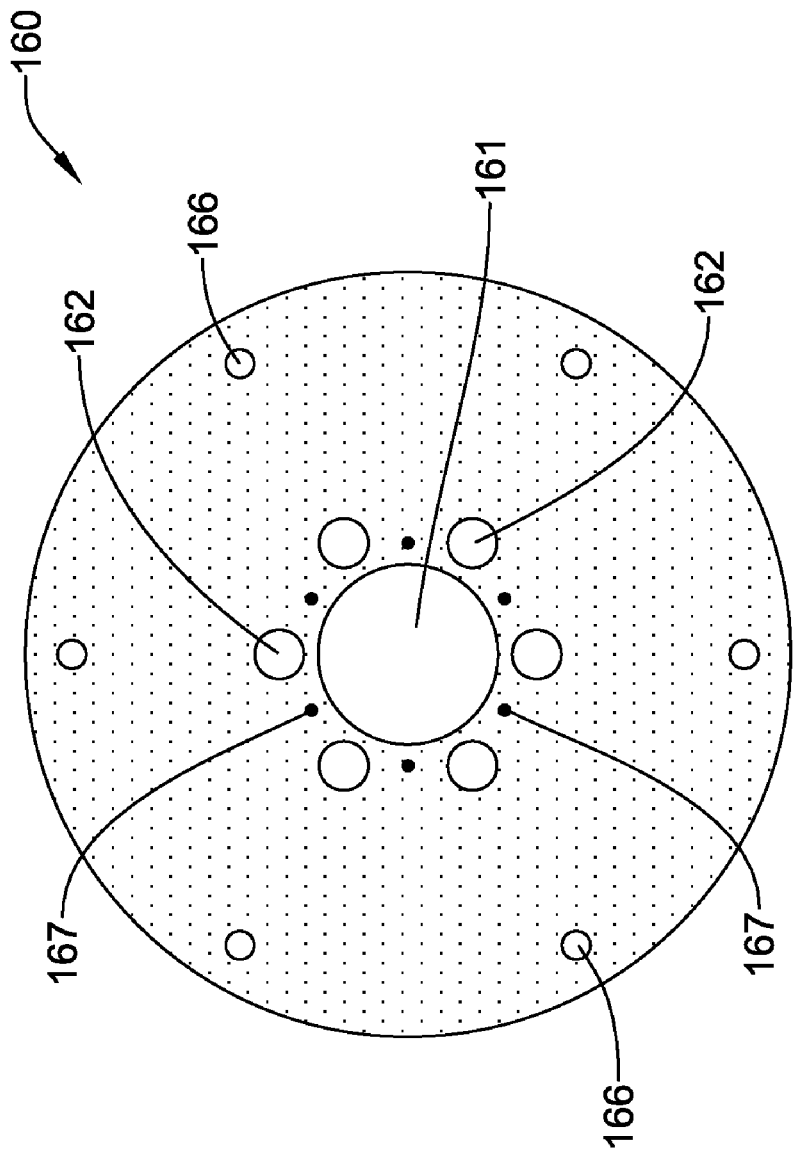

FIG. 19 shows a flexible elastomeric body 160. The flexible elastomeric body 160 includes a central crimping lumen 161 longitudinally extending through at least a portion of the length of the flexible elastomeric body 160. A plurality of inflation lumens 162 may be positioned around the crimping lumen 161. For example, the inflation lumens 162 may be arranged in a radial array around the crimping lumen 161. In addition to the inflation lumens 162, a plurality of rigid members 167, such as metallic tubes and/or rods, may longitudinally extend along the flexible elastomeric body 160 in a radial array around the crimping lumen 161. The rigid members 167 may be formed with the flexible elastomeric body 160 during an extrusion or molding process, for example, or the rigid members 167 may be placed in the flexible elastomeric body 160 subsequent to forming the flexible elastomeric body 160. The rigid members 167 may facilitate crimping a stent onto a balloon by adding rigidity to the flexible elastomeric body 160 as the crimping lumen 161 is in conforming contact around the stent.

The flexible elastomeric body 160 may also include a plurality of expansion rod lumens 166, similar to the expansion rod lumens 36 of the flexible elastomeric body 22. The expansion rod lumens 166 may be radially arranged around the flexible elastomeric body 160 in order to facilitate elastically stretching the flexible elastomeric body 160 radially outward.

Another exemplary method of crimping a balloon to a stent using a flexible elastomeric body will now be described while referring to FIGS. 20A-20E. The method described uses a mechanical force instead of a pressurized fluid to generate the crimping force necessary to crimp a stent onto a catheter balloon.

FIG. 20A is an end view of a crimping fixture 220 including a flexible elastomeric body 222. Similar to the flexible elastomeric body 22, the flexible elastomeric body 222 may be formed of a suitable elastomeric material, including, but not necessarily limited to, those materials listed above with regard to the flexible elastomeric body 22.

The flexible elastomeric body 222 may include a crimping lumen 230 defined by an inner surface 232 of the flexible elastomeric body 222. As discussed in more detail herein, the crimping lumen 230 may accommodate a stent during a crimping process. In some embodiments the crimping lumen 230 may be centrally located along a central longitudinal axis of the flexible elastomeric body 222. In some embodiments, the crimping lumen 230 may longitudinally extend from a first end of the flexible elastomeric body 222 to a second end of the flexible elastomeric body 222. In other embodiments, the crimping lumen 230 may longitudinally extend from a first end of the flexible elastomeric body 222 toward a second end of the flexible elastomeric body 222, but not all the way to the second end of the flexible elastomeric body 222. In still other embodiments, the crimping lumen 230 may longitudinally extend from a second end of the flexible elastomeric body 222 toward a first end of the flexible elastomeric body 222, but not all the way to the first end of the flexible elastomeric body 222.

The crimping fixture 220 may also include a plurality of arms 240, or other means for radially stretching the flexible elastomeric body 222. The arms 240 may be arranged in a radial array around the flexible elastomeric body 222, and may be attached to the flexible elastomeric body 222 by expansion rods, similar to those discussed regarding the crimping fixture 20, or by other suitable means. Outward radial actuation of the arms 240 may radially stretch the flexible elastomeric body 222 radially outward, whereas, inward radial actuation of the arms 240 may radially relax the flexible elastomeric body 222 radially inward.

Figure 20B:
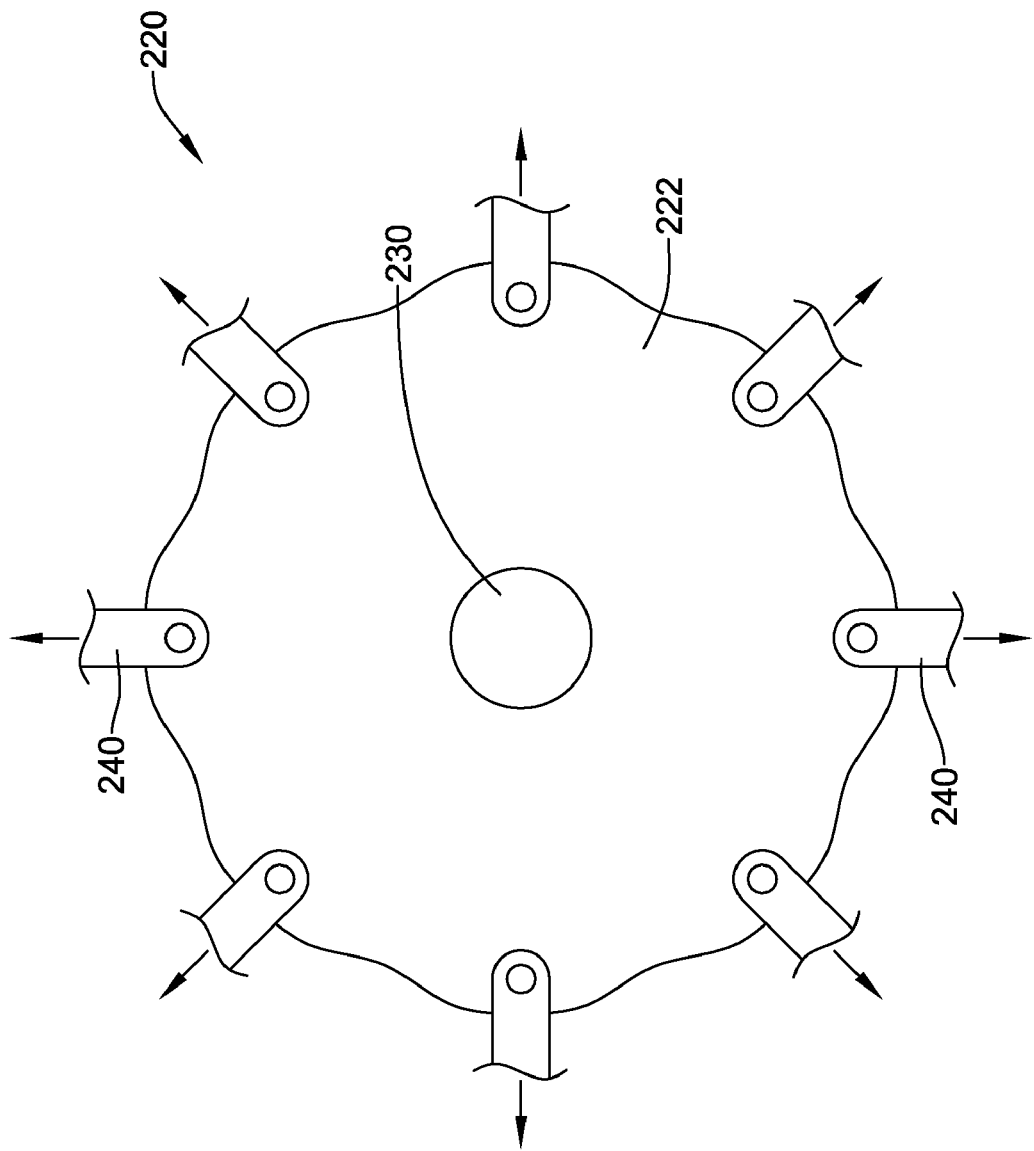

FIG. 20A shows the flexible elastomeric body 222 in a relaxed, unstretched state, and FIG. 20B shows the flexible elastomeric body 222 in an elastically stretched or expanded state. As shown in FIG. 20A, the plurality of arms 240 may be arranged in a radial array around the flexible elastomeric body 222. When the arms 240 are actuated radially outward, the flexible elastomeric body 222 is elastically stretched or expanded as shown in FIG. 20B. The arrows of FIG. 20B illustrate the arms 240 actuating radially outward. When the flexible elastomeric body 222 is elastically stretched or expanded, the cross-sectional dimension (e.g., diameter) of the crimping lumen 230 is increased in size. In some embodiments, the crimping lumen 230 may be increased from a diameter of less than 0.045 inches in the relaxed, unstretched state to a diameter of greater than 0.060 inches in the elastically stretched or expanded state. Other comparative dimensions are also possible in which the diameter of the crimping lumen 230 in the relaxed, unstretched state is less than the diameter of the crimping lumen 230 in the elastically stretched or expanded state. In some embodiments, the diameter of the crimping lumen 230 in the elastically stretched or expanded state may be 200% or more, 250% or more, or 300% or more than the diameter of the crimping lumen 230 in the relaxed, unstretched state.

In the relaxed, unstretched state, the diameter of the crimping lumen 230 may be less than the outside diameter of a stent subsequent to crimping the stent onto a balloon catheter. In other words, the diameter of the crimping lumen 230 in the relaxed, unstretched state may be less than the diameter of a post-crimped stent. In the elastically stretched, expanded state, the diameter of the crimping lumen 230 may be greater than the outside diameter of a stent prior to crimping the stent onto a balloon. In other words, the diameter of the crimping lumen 230 in the elastically stretched, expanded state may be greater than the diameter of a pre-crimped stent.

During a crimping process, the flexible elastomeric body 222 may be elastically stretched from the relaxed, unstretched state of FIG. 20A to the elastically stretched or expanded state of FIG. 20B. For example, actuation means may be actuated to radially expand the arms 240 of the crimping fixture 220 radially outward. Outward radial actuation of the arms 240 stretches the flexible elastomeric body 222 in order to enlarge the crimping lumen 230 for placement of a pre-crimped stent therein.

Figure 20C:
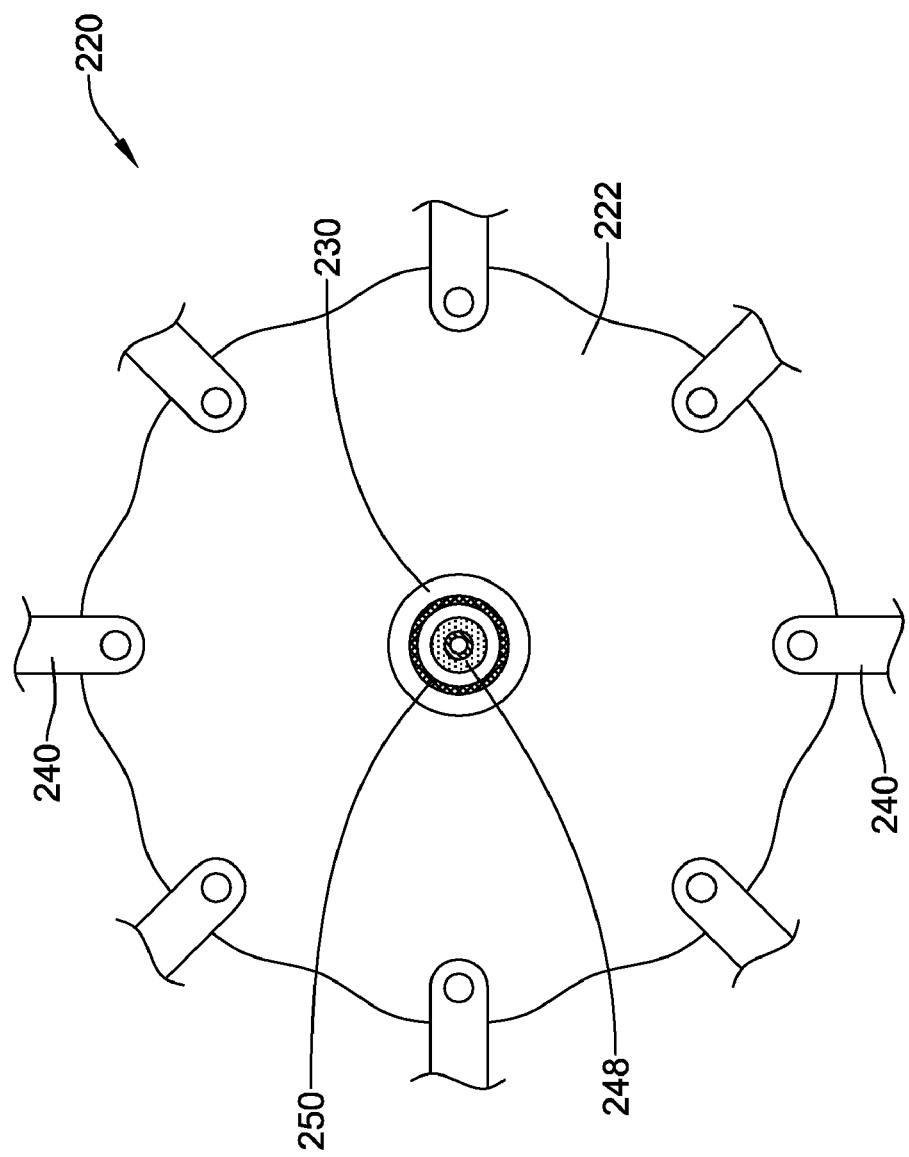

After the flexible elastomeric body 222 is elastically stretched such that the crimping lumen 230 is enlarged to a diameter greater than the diameter of a pre-crimped stent, a pre-crimped stent 250, having an outside diameter less than the enlarged diameter of the crimping lumen 230, may be positioned in the crimping lumen 230, as shown in FIG. 20C.

Additionally, a balloon 248 attached to a catheter shaft, which may be a folded, deflated or partially deflated balloon, of a catheter may be positioned through the pre-crimped stent 250. In some embodiments, the pre-crimped stent 250 may be loaded onto the balloon 248 prior to positioning the stent 250 within the crimping lumen 230. In some embodiments, the pre-crimped stent 250 may be positioned within the crimping lumen 230 such that the pre-crimped stent 250 is completely surrounded by the crimping lumen 230. For example, the entire length of the pre-crimped stent 250 may be positioned between the first and second ends of the flexible elastomeric body 222.

With the pre-crimped stent 250 and the balloon 248 positioned within the crimping lumen 230, the arms 240 may be radially actuated inward toward the crimping lumen 230. Inward actuation of the arms 240 allows the flexible elastomeric body 222 to be partially relaxed around the pre-crimped stent 250. However, it is noted that in the partially relaxed state, the flexible elastomeric body 222 remains in tension as the pre-crimped stent 250 prevents the flexible elastomeric body 222 from returning to the relaxed, unstretched state shown in FIG. 20A. Thus, as the flexible elastomeric body 222 remains in tension, the inner surface 232 of the crimping lumen 230 tends to conform to the outer surface of the pre-crimped stent 250, applying an inward force on the pre-crimped stent 250.

Figure 20D:
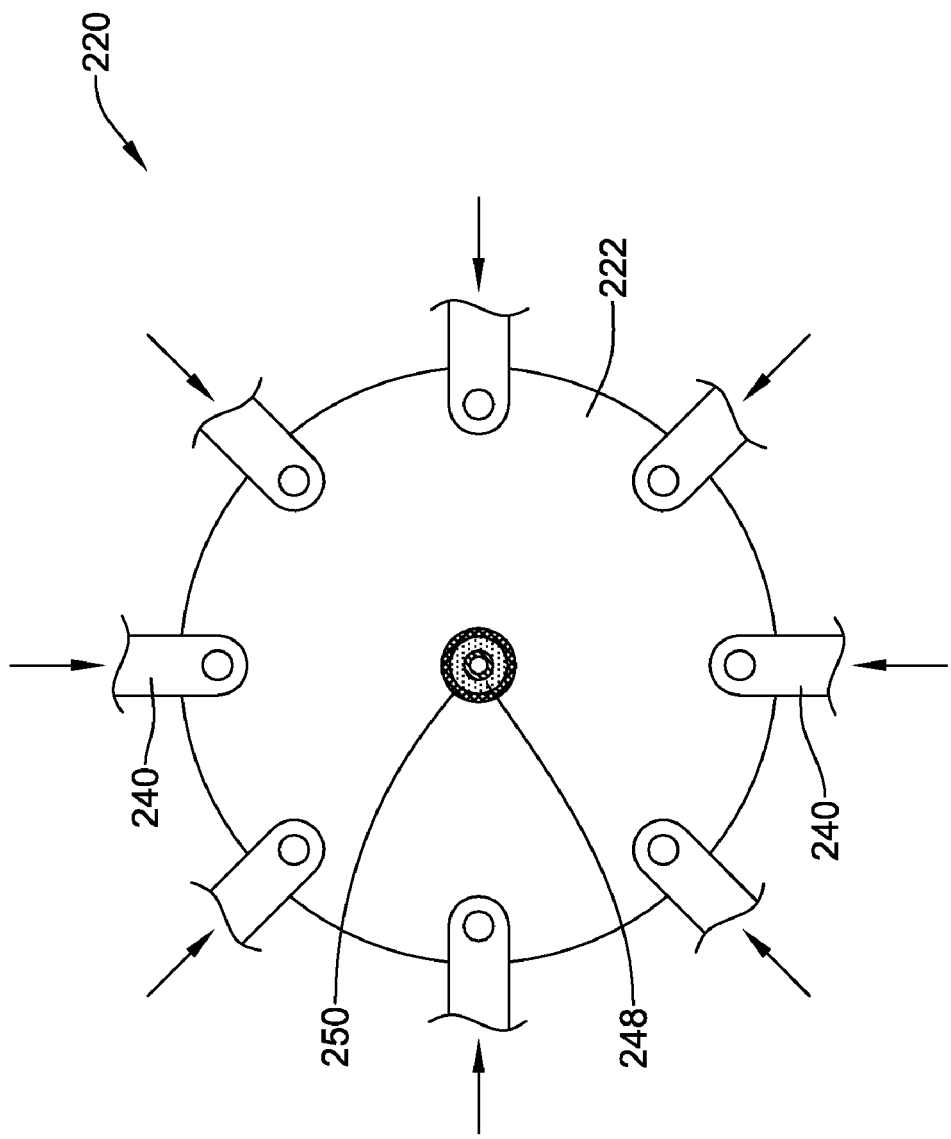

Additional inward radial retraction of the arms 240 may increase the force being applied to the stent 250 causing the stent to be compressed to a smaller outside diameter, thereby crimping the stent 250 to the balloon 248, as shown in FIG. 20D. As the stent 250 is compressed or crimped to a smaller outside diameter, the inner surface 232 of the crimping lumen 230 remains in conforming contact with the outside diameter of the stent 250, as the flexible elastomeric body 222 remains in tension throughout the application of the radially inward mechanical force. As the inner surface 232 of the crimping lumen 230 remains in conforming contact with the outside diameter of the stent 250, the stent 250 is subjected to omnidirectional forces providing uniform crimping of the stent 250 to the balloon 248.

At the completion of the crimping process, the stent 250 may be crimped to a post-crimped diameter less than the pre-crimped diameter of the stent 250. However, the post-crimped diameter of the stent 250 may be larger than the diameter of the crimping lumen 230 of the flexible elastomeric body 222 when the flexible elastomeric body 222 is in the relaxed, unstretched state. Thus, it can be seen that at the conclusion of crimping the stent 250 to a smaller, crimped diameter, the flexible elastomeric body 222, conforming around the periphery of the stent 250, remains in elastic tension. Thus, in some embodiments, the flexible elastomeric body 222 is never placed in compression during the crimping process.

Once the stent 250 has been crimped to the balloon 248 of the catheter, the flexible elastomeric body 222 may again be elastically stretched. For example, the arms 240 of the crimping fixture 220 may be actuated to radially expand the flexible elastomeric body 222. Outward radial actuation of the arms 240 stretches the flexible elastomeric body 222 in order to enlarge the crimping lumen 230 for removal of a crimped stent 250 and/or the placement of another pre-crimped stent 250 therein.

Figure 21:
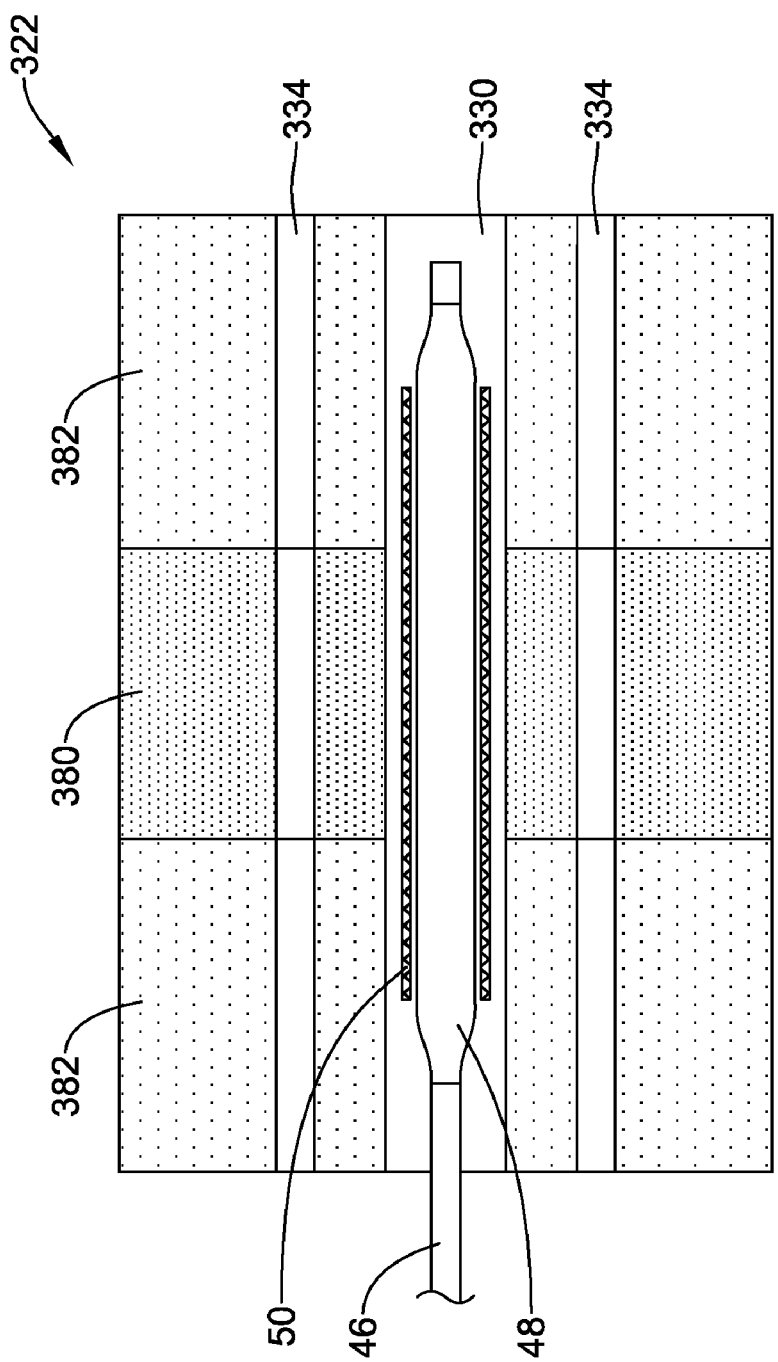
FIG. 21 is longitudinal cross-sectional view of an alternative flexible elastomeric body.

FIG. 21 is a longitudinal cross-sectional view of an alternative embodiment of a flexible elastomeric body 322 for use in crimping a stent 50 onto a balloon 48 of a catheter 46. The flexible elastomeric body 322 may include a crimping lumen 330 (shown with a stent 50 and a balloon 48 of a catheter 46 positioned within the crimping lumen 330), similar to the crimping lumen 30 of the flexible elastomeric body 22.

The flexible elastomeric body 322 may also include a plurality of inflation lumens 334 longitudinally extending through the flexible elastomeric body 322 at located radially outward of the crimping lumen 330.

As shown in FIG. 21, the flexible elastomeric body 322 may include two or more regions of material having different flexibility, elasticity, and/or hardness characteristics. For example, the flexible elastomeric body 322 may include a central portion 380 formed of a first material having a first flexibility, elasticity and/or hardness. The flexible elastomeric body 322 may also include end portions 382 located on either side of the central portion 380 formed of a second material having a second flexibility, elasticity and/or hardness different from the flexibility, elasticity and/or hardness of the first material. In some embodiments the first material may have a flexibility, elasticity and/or hardness greater than the second material, while in other embodiments the first material may have a flexibility, elasticity and/or hardness less than the second material.

In other embodiments, the regions of differing flexibility, elasticity and/or hardness may extend longitudinally along the flexible elastomeric body 322 from the first end of the elastomeric body 322 to the second end of the elastomeric body. For example, a first region of differing flexibility, elasticity and/or hardness may longitudinally or axially extend from the first end of the elastomeric body 322 to the second end of the elastomeric body 322 at a first radial position; a second region of differing flexibility, elasticity and/or hardness may longitudinally or axially extend from the first end of the elastomeric body 322 to the second end of the elastomeric body 322 at a second radial position; a third region of differing flexibility, elasticity and/or hardness may longitudinally or axially extend from the first end of the elastomeric body 322 to the second end of the elastomeric body 322 at a third radial position, etc.

The difference in flexibility, elasticity and/or hardness of the two or more regions of material of the flexible elastomeric body 322 may provide the flexible elastomeric body 322 with desired crimping characteristics. For example, as shown in FIG. 21, the central portion 380 may apply greater crimping forces to the central portion of the stent 50 than the crimping forces applied to the outer ends of the stent 50 by the end portions 382 of the flexible elastomeric body 322. In other embodiments, the end portions 382 may apply greater crimping forces to the outer ends of the stent 50 than the crimping forces applied to the central portion of the stent 50 by the central portion 380 of the flexible elastomeric body 322.

Figure 22:
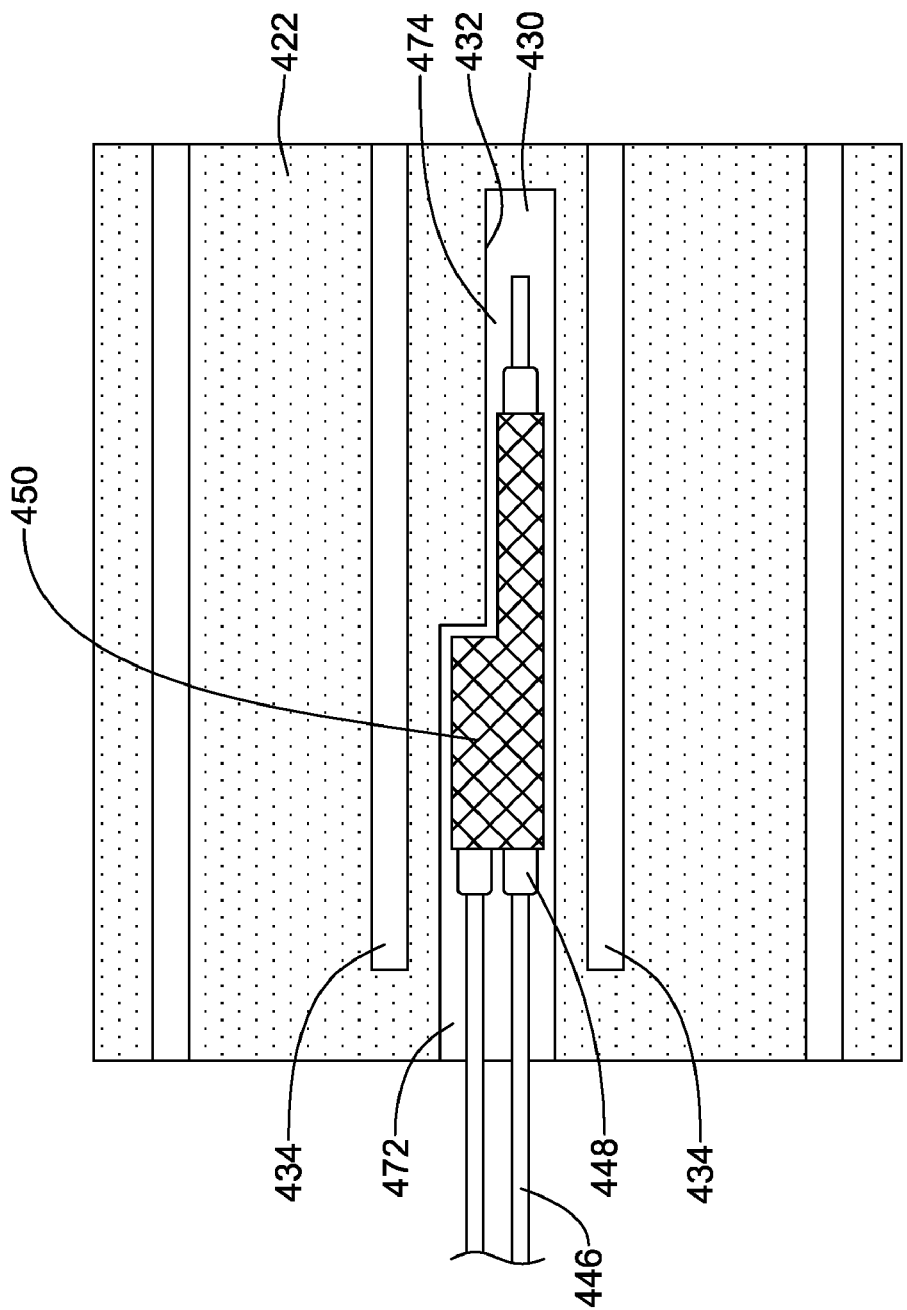
FIG. 22 is a longitudinal cross-sectional view of another alternative flexible elastomeric body.

FIG. 22 is longitudinal cross-sectional view of an alternative embodiment of a flexible elastomeric body 422 for use in crimping a stent 450 onto a balloon 448 of a catheter 446. The flexible elastomeric body 422 may include a crimping lumen 430 (shown with a stent 450 and a balloon 448 of a catheter 446 positioned within the crimping lumen 430).

The flexible elastomeric body 422 may also include a plurality of inflation lumens 434 longitudinally extending through the flexible elastomeric body 422 at located radially outward of the crimping lumen 430.

As shown in FIG. 22, the crimping lumen 430 may have a non-uniform profile or diameter. For example, the crimping lumen 430 may have a first section 472 having a first cross-sectional shape and/or dimension (e.g., diameter) and a second section 474 having a second cross-sectional shape and/or dimension (e.g., diameter) different from the first cross-sectional shape and/or dimension of the first section 472. For instance, the first section 472 of the crimping lumen 430 may have a first diameter and the second section 474 of the crimping lumen 430 may have a second diameter less than the diameter of the first section 472. Such a crimping lumen 430 may be adapted for receiving a bifurcated stent 450. Thus, when attempting to crimp a bifurcated stent 450 (or other irregular shaped stent) onto a balloon 448, the inner peripheral surface 432 of the crimping lumen 430 may approximate the shape of the outer surface of the bifurcated stent 450.

Figure 23:
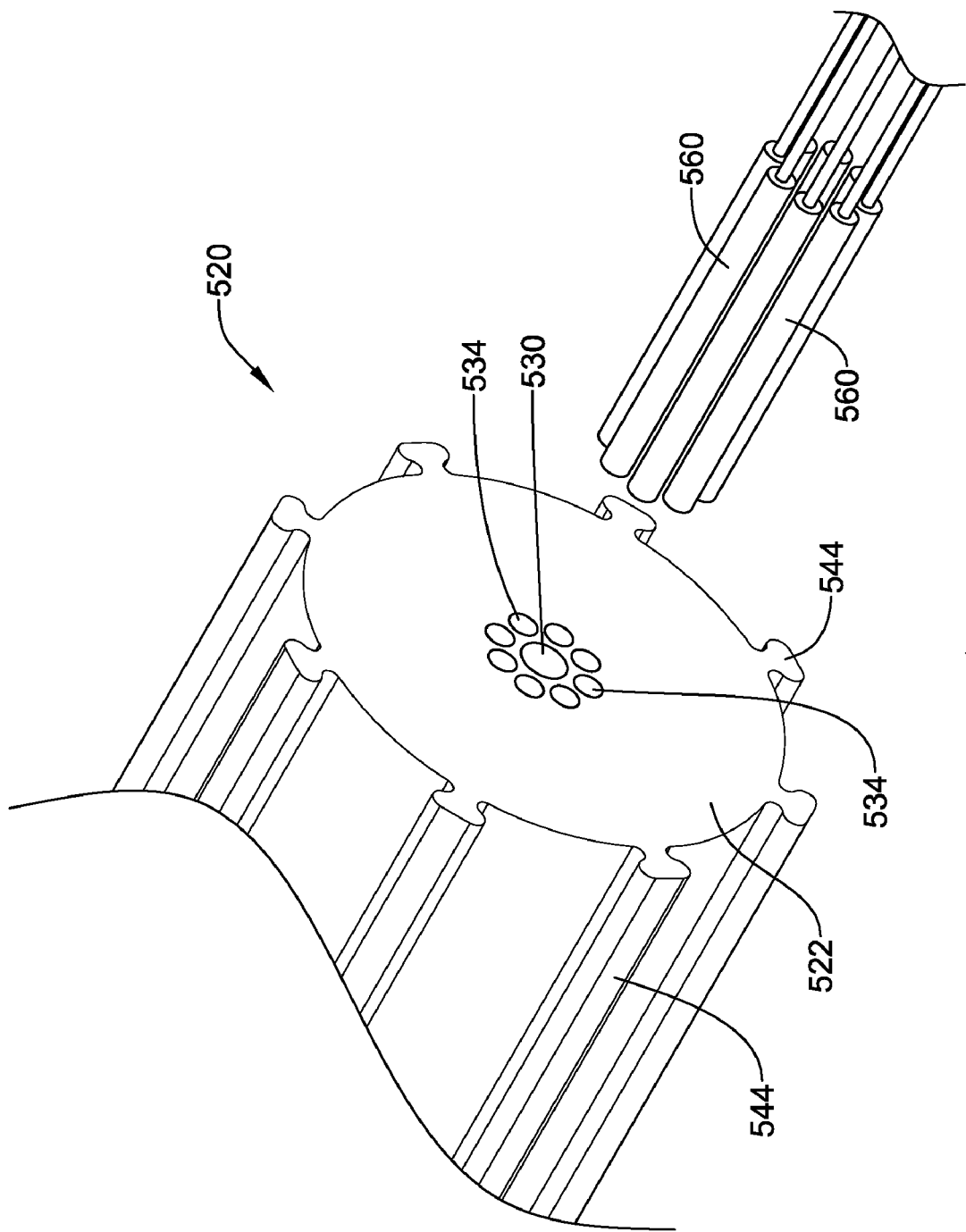
FIG. 23 is perspective view an exemplary embodiment of a crimping fixture including a plurality of removable bladders.

An alternative embodiment of a crimping fixture 520 is shown in FIG. 23. The crimping fixture 520 includes a flexible elastomeric body 522, similar to the flexible elastomeric body 22. The flexible elastomeric body 522 may be formed of any suitable elastomeric material, including, but not necessarily limited to, the materials listed above regarding the flexible elastomeric body 22.

The flexible elastomeric body 522 also may include a plurality of projections 544 extending radially from the flexible elastomeric body. The projections 544 may be used in order to elastically stretch the flexible elastomeric body 522 during a crimping process. It is noted that other means of radially stretching the flexible elastomeric body 522 may also be utilized.

The flexible elastomeric body 522 may include a crimping lumen 530 and a plurality of inflation lumens 534 surrounding the crimping lumen 530. Instead of directly inflating the inflation lumens 534, the crimping fixture 520 may include a plurality of removable bladders 560 which may be selectively inserted into the inflation lumens 534. The removable bladders 560 may be individually or collectively inflated, as desired, to impart inward crimping forces on a stent disposed within the crimping lumen 530 of the flexible elastomeric body 522.

Figure 2:
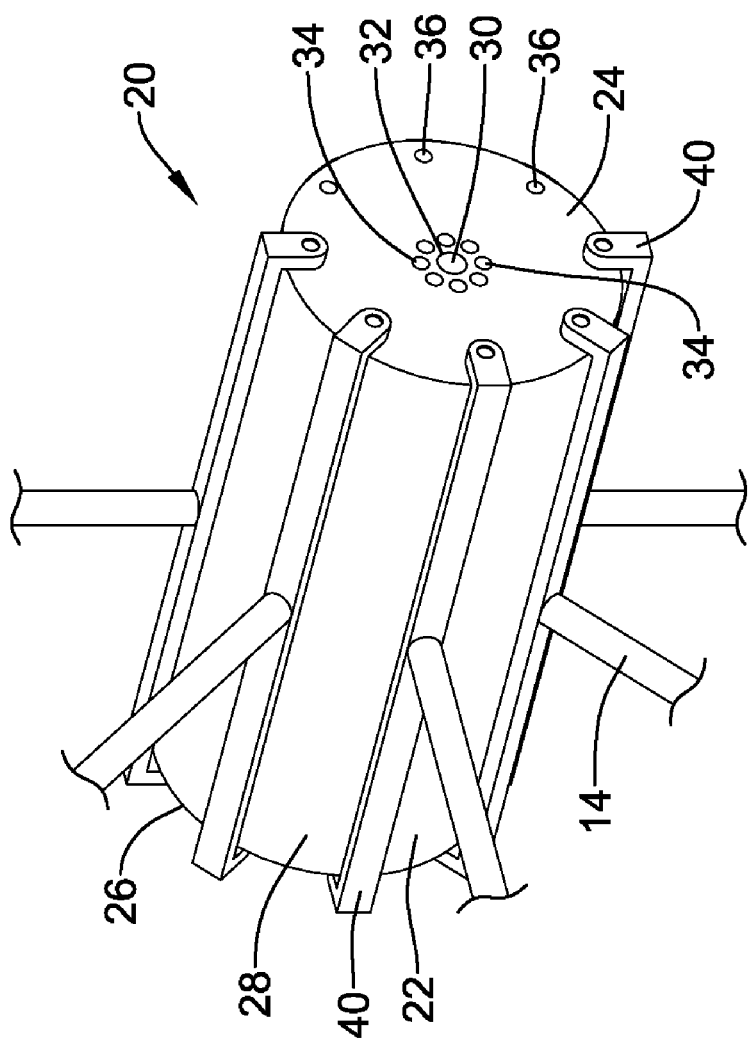
FIG. 2 is a perspective view of an illustrative stent crimping fixture for use in the stent crimping machine of FIG. 1.
Figure 24:
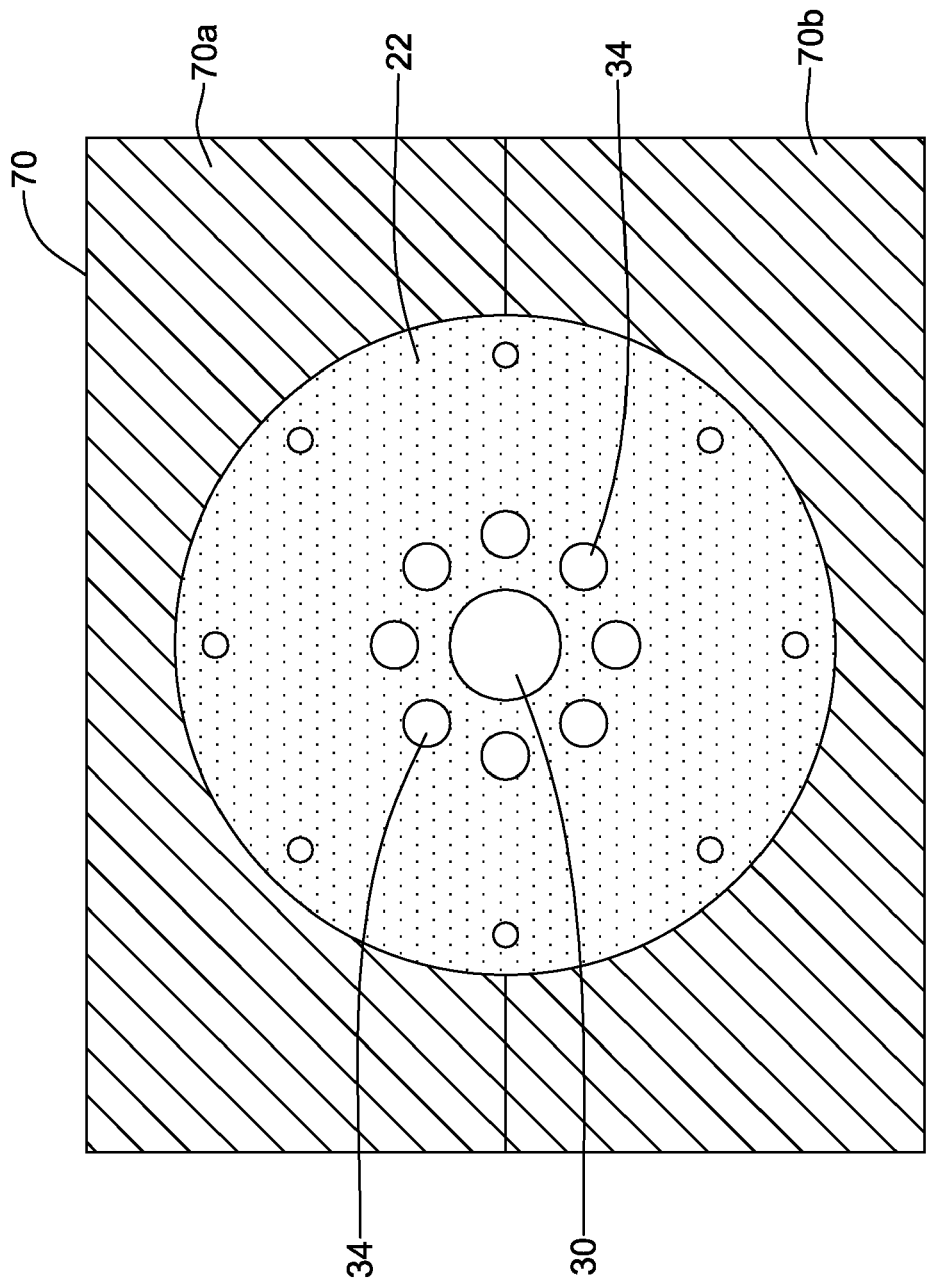
FIG. 24 is an alternative stent crimping fixture including a rigid enclosure around the flexible elastomeric body.

FIG. 24 illustrates an alternative arrangement of the flexible elastomeric body 22 of FIG. 2 used in a crimping process. As shown in FIG. 24, prior to inflating the inflation lumens 34 with a pressurized fluid, the flexible elastomeric body 22 may be enclosed within a rigid chamber 70. As shown in FIG. 24, the rigid chamber 70 may have a top section 70a and a bottom section 70b, or additional sections as desired. Each section 70a/70b may have a cavity for placing the flexible elastomeric body 22 therein. The rigid chamber 70 may be significantly more rigid than the flexible elastomeric body 22. Thus, when the inflation lumens 34 are inflated with a pressurized fluid the flexible elastomeric body 22 is prevented from expanding outward by the presence of the rigid chamber 70. Therefore, force generated from the pressurized fluid may be more immediately and/or fully directed to the stent 50 located in the crimping lumen 30.

Figure 25:
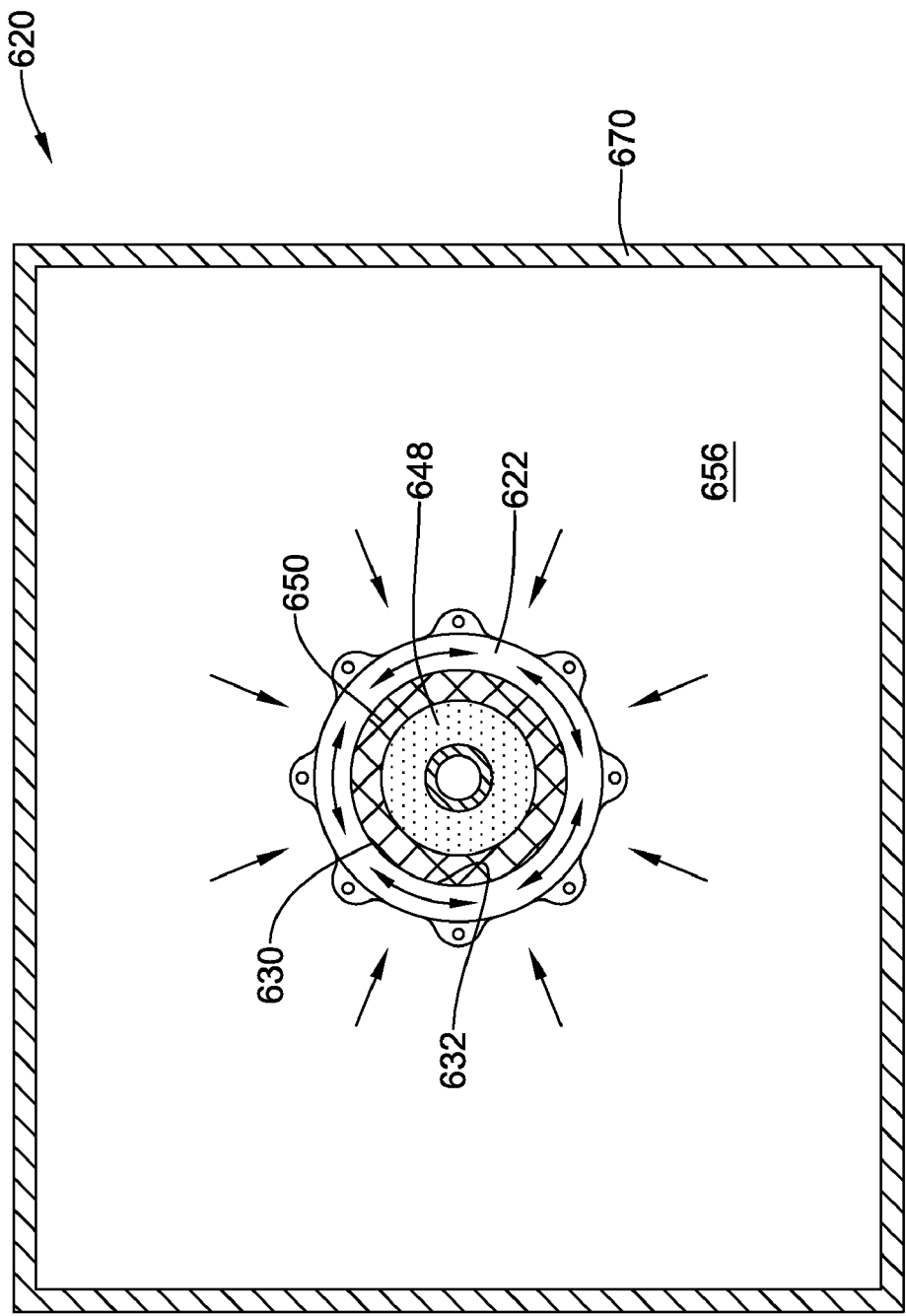
FIG. 25 is another alternative stent crimping fixture including a pressure chamber.

Yet, another alternative of a stent crimping fixture 620 is shown in FIG. 25. The stent crimping fixture 620 includes a flexible elastomeric body 622 and a pressure chamber 670. During a crimping process, the flexible elastomeric body 622 may be radially stretched outward to enlarge the central crimping lumen 630 of the flexible elastomeric body 622. A stent 650 may be positioned within the crimping lumen 630, and the flexible elastomeric body 622 may then be allowed to contract around the pre-crimped stent 650. With the flexible elastomeric body 622 in a partially relaxed state around the pre-crimped stent 650, the flexible elastomeric body 622 remains in tension as the pre-crimped stent 650 prevents the flexible elastomeric body 622 from returning to a relaxed, unstretched state. Thus, as the flexible elastomeric body 622 remains in tension, the inner surface 632 of the crimping lumen 630 tends to conform to the outer surface of the pre-crimped stent 650, applying an inward force on the pre-crimped stent 650.

The pre-crimped stent 650, with the flexible elastomeric body 622 in conformal contact with the pre-crimped stent 650, may be positioned in the pressure chamber 670. A pressurized fluid 656 may be introduced into the pressure chamber 670, creating an inward force acting on the stent 650. The radial compressive force may be transformed into an omni-directional crimping force, normal to the stent 650 at all points of surface contact between the inner surface 632 of the crimping lumen 630 and the outer surface of the stent 650. The inward force created by the pressurization of the pressure chamber 670 causes the stent 650 to be compressed to a smaller outside diameter, thereby crimping the stent 650 to the balloon 648. As the stent 650 is compressed or crimped to a smaller outside diameter, the inner surface 632 of the crimping lumen 630 remains in conforming contact with the outside diameter of the stent 650, as the flexible elastomeric body 622 remains in tension throughout the application of fluid pressurization of the pressure chamber 670. As the inner surface 632 of the crimping lumen 630 remains in conforming contact with the outside diameter of the stent 650, the stent 650 is subjected to iso-static fluid pressure (e.g., subjected to equal pressure from every side, or contact point).

A pressurized fluid 656 may be continued to be applied until a desired degree of crimping has been attained. For example, in some embodiments a pressure control system may be used to monitor the crimping process, similar to the pressure control system described above. Once a predetermined time of applying pressure and/or a predetermined size of the crimped stent 650 has been attained, the pressure within the pressure chamber 670 may be reduced and/or the pressurized fluid 656 may be removed from the pressure chamber 670.

At the completion of the pressurization of the pressure chamber 670 during the crimping process, the stent 650 may be crimped onto the balloon 648 to a crimped diameter greater than the diameter of the crimping lumen 630 of the flexible elastomeric body 622 in the relaxed, unstretched state. Thus, it can be seen that at the conclusion of crimping the stent 650 to a smaller, crimped diameter, the flexible elastomeric body 622, conforming around the periphery of the stent 650, remains in elastic tension. Thus, in some embodiments, the flexible elastomeric body 622 is never placed in compression during the crimping process.

Once the stent 650 has been crimped to the balloon 648 of the catheter, the flexible elastomeric body 622 may again be elastically stretched in order to enlarge the crimping lumen 630 for removal of a crimped stent 650 and/or the placement of another pre-crimped stent 650 therein.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A crimping fixture for crimping a stent onto a balloon of a catheter, the stent having a pre-crimped diameter and a pre-crimped perimeter prior to being subjected to a crimping process, the crimping fixture comprising:

an elongate body having a first end and a second end, the elongate body formed of an elastomeric material allowing elastic deformation of the elongate body;

the elongate body including a crimping lumen having a diameter and a peripheral surface;

the elongate body further including one or more inflation lumens spaced around the crimping lumen;

wherein the elastomeric material allows the elongate body to be elastically radially stretched in order to increase the diameter of the crimping lumen to receive the stent therein.

2. The crimping fixture of claim 1, wherein the peripheral surface of the crimping lumen of the elongate body substantially conforms to the pre-crimped perimeter of the stent.

3. The crimping fixture of claim 1, wherein the elastomeric material has an elastic deformation of at least 300%.

4. The crimping fixture of claim 1, further comprising a means for elastically stretching the elongate body.

5. The crimping fixture of claim 4, wherein the means for elastically stretching the elongate body includes a plurality of expansion rods extending through the elongate body.

6. The crimping fixture of claim 1, wherein the elongate body further includes one or more rigid members located in the elongate body to direct crimping forces to the stent.

7. A crimping member for crimping a stent having a pre-crimped diameter onto a balloon of a catheter, the crimping member comprising:
 an elongate body having a first end, a second end, and an outer peripheral surface extending between the first end and the second end, the elongate body formed of an elastomeric material which may be elastically stretched between a relaxed state in which the elongate body is not placed in tension and an elastically stretched state in which the elongate body is placed in tension;
 the elongate body including a crimping lumen, wherein the crimping lumen has a first diameter in the relaxed state and a second diameter larger than the first diameter in the elastically stretched state;
 wherein the first diameter of the crimping lumen of the elongate body is less than the pre-crimped diameter of a stent for placement therein; and
 a plurality expansion rods radially arranged around the elongate body configured to be mechanically actuated radially outward in order to elastically stretch the elongate body to the elastically stretched state.

8. The crimping member of claim 7, wherein the elastomeric material has an elastic deformation of at least 300%.

9. A crimping member for crimping a stent having a pre-crimped diameter onto a balloon of a catheter, the crimping member comprising:
 an elongate body having a first end, a second end, and an outer peripheral surface extending between the first end and the second end, the elongate body formed of an elastomeric material which may be elastically stretched between a relaxed state in which the elongate body is not placed in tension and an elastically stretched state in which the elongate body is placed in tension;
 the elongate body including a crimping lumen, wherein the crimping lumen has a first diameter in the relaxed state and a second diameter larger than the first diameter in the elastically stretched state;
 wherein the first diameter of the crimping lumen of the elongate body is less than the pre-crimped diameter of a stent for placement therein; and
 wherein the elongate body further includes a plurality of inflation lumens spaced around the crimping lumen.

10. The crimping member of claim 9, wherein the crimping lumen extends from the first end toward the second end of the elongate body, but not all the way to the second end of the elongate body, and the plurality of inflation lumens extend from the second end of the elongate body, but not all the way to the first end of the elongate body.

11. An assembly for crimping a stent to a balloon of a catheter, the assembly comprising:
 a catheter including an elongate shaft and a balloon secured to a distal region of the elongate shaft;
 a stent having a pre-crimped diameter, the stent loaded onto the balloon; and
 a crimping member including an elongate body formed of an elastomeric material which may be elastically stretched between a relaxed state in which the crimping member is not placed in tension and an elastically stretched state in which the crimping member is placed in tension;
 the elongate body of the crimping member including a crimping lumen for receiving the stent loaded onto the balloon of the catheter, the crimping lumen having a first diameter in the relaxed state and a second diameter larger than the first diameter in the elastically stretched state;
 wherein the first diameter of the crimping lumen of the elongate body is less than the pre-crimped diameter of the stent;
 the crimping member further including a plurality expansion rods radially arranged around the elongate body configured to be mechanically actuated radially outward in order to elastically stretch the elongate body to the elastically stretched state.

12. The assembly of claim 11, wherein when the stent is positioned in the crimping lumen of the elongate body, the crimping member remains in tension.

13. The assembly of claim 11, wherein the elastomeric material has an elastic deformation of at least 300%.

14. An assembly for crimping a stent to a balloon of a catheter, the assembly comprising:
 a catheter including an elongate shaft and a balloon secured to a distal region of the elongate shaft;
 a stent having a pre-crimped diameter, the stent loaded onto the balloon; and
 a crimping member including an elongate body formed of an elastomeric material which may be elastically stretched between a relaxed state in which the crimping member is not placed in tension and an elastically stretched state in which the crimping member is placed in tension;
 the elongate body of the crimping member including a crimping lumen for receiving the stent loaded onto the balloon of the catheter and one or more inflation lumens spaced around the crimping lumen, the crimping lumen having a first diameter in the relaxed state and a second diameter larger than the first diameter in the elastically stretched state;
 wherein the first diameter of the crimping lumen of the elongate body is less than the pre-crimped diameter of the stent; and
 wherein the one or more inflation lumens may be pressurized to exert an inward crimping force on the stent to crimp the stent to the balloon.

* * * * *